(12) United States Patent
Howarth et al.

(10) Patent No.: US 7,455,859 B2
(45) Date of Patent: *Nov. 25, 2008

(54) HIGHLY CONCENTRATED BROMINE COMPOSITIONS AND METHODS OF PREPARATION

(75) Inventors: Jonathan N. Howarth, Modesto, CA (US); Michael S. Harvey, Modesto, CA (US)

(73) Assignee: Enviro Tech Chemical Services, Inc., Modesto, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 11/341,022

(22) Filed: Jan. 27, 2006

(65) Prior Publication Data

US 2006/0188429 A1 Aug. 24, 2006

Related U.S. Application Data

(63) Continuation of application No. 10/609,280, filed on Jun. 27, 2003, now Pat. No. 7,045,153.

(51) Int. Cl.
*A01N 59/00* (2006.01)
(52) U.S. Cl. .................. 424/661; 210/755; 210/764; 424/722; 424/723
(58) Field of Classification Search .............. 424/723
See application file for complete search history.

(56) References Cited

U.S. PATENT DOCUMENTS

| | | | | |
|---|---|---|---|---|
| 2,705,670 A * | 4/1955 | Chao | .......................... | 423/482 |
| 3,558,503 A * | 1/1971 | Goodenough et al. | ..... | 252/187.2 |
| 4,992,209 A * | 2/1991 | Smyk et al. | .................. | 252/387 |
| 5,464,636 A * | 11/1995 | Hight et al. | ................. | 424/661 |
| 6,007,726 A * | 12/1999 | Yang et al. | ................... | 210/752 |
| 6,322,822 B1 * | 11/2001 | Moore, Jr. et al. | ........... | 424/703 |
| 6,506,418 B1 * | 1/2003 | McKinnie et al. | ........... | 424/703 |
| 6,660,307 B2 * | 12/2003 | Zolotarsky et al. | .......... | 424/703 |
| 6,669,904 B1 * | 12/2003 | Yang et al. | ..................... | 422/37 |
| 7,045,153 B2 * | 5/2006 | Howarth et al. | .............. | 424/723 |
| 7,087,251 B2 * | 8/2006 | Nalepa | ....................... | 424/703 |
| 7,309,503 B2 * | 12/2007 | Howarth et al. | ............. | 424/723 |
| 2004/0120853 A1 * | 6/2004 | Carpenter et al. | ............. | 422/37 |

* cited by examiner

*Primary Examiner*—Peter A. Hruskoci
(74) *Attorney, Agent, or Firm*—Audrey A. Millemann; Weintraub Genshlea Chediak

(57) ABSTRACT

Liquid and solid bromine-containing compositions are described. A liquid mixed halogen composition is also described. The highly concentrated liquid compositions and the high-activity solid compositions have excellent physical and chemical stability. The compositions are effective biocides in water treatment. Methods of preparing the compositions are also disclosed. These include combining a bromine compound in the oxidation state of −1 with hydrogen peroxide and a complexing agent followed by the addition of an alkaline source. The methods may further include the use of a solid organic or solid inorganic halogenating agent, conducting a solid-liquid separation, and adding an alkaline source.

7 Claims, No Drawings

HIGHLY CONCENTRATED BROMINE COMPOSITIONS AND METHODS OF PREPARATION

CROSS-REFERENCE TO RELATED APPLICATION

This application is a continuation of U.S. application Ser. No. 10/609,280, filed on Jun. 27, 2003, now U.S. Pat. No. 7,045,153.

BACKGROUND OF THE INVENTION

1. Field of the Invention

The invention relates to liquid and solid bromine-containing compositions, and a liquid mixed halogen bromine and chlorine-containing composition, for use as biocides in water treatment. The highly concentrated liquid compositions and high-activity solid compositions have excellent physical and chemical stability. The invention also relates to methods of preparing the liquid and solid compositions.

2. Description of the Related Art

There are many ways of delivering a biocidal dose of bromine into water systems where the growth of microorganisms must be controlled. Early examples of accomplishing this involved introducing elemental liquid bromine ($Br_2$) or liquid bromine chloride (BrCl) to the water requiring treatment. However, both liquids are very volatile and evolve copious amounts of highly toxic and corrosive bromine fumes under normal conditions. Therefore, elaborate and expensive storage, transportation and handling safeguards must be practiced when using these products. It is hardly surprising that the high costs of managing these hazardous properties have rendered the use of elemental liquid bromine and liquid bromine chloride obsolete in most water disinfection applications.

An alternative system that overcomes these limitations employs an aqueous solution of sodium bromide (NaBr) in conjunction with liquid sodium hypochlorite (NaOCl) bleach. The user feeds the two materials to a common point where the NaOCl oxidizes the bromide ion to yield a mixture of hypobromous acid (HOBr) and hypobromite ($OBr^-$)ion. This activated solution must then be quickly introduced to the water being treated because the species in solution are unstable to the following rapid disproportionation and decomposition reactions.

Disproportionation: $2HOBr+OBr^-=BrO_3^-+2HBr$

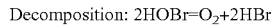
Decomposition: $2HOBr=O_2+2HBr$

Such reactions are undesirable because the products of the reactions (HBr, $O_2$ and $BrO_3^-$) are not biocidally active.

Many users of this technology indicate that metering of two separate solutions of NaBr and NaOCl is especially inconvenient since two sets of pumps, flowmeters, valves, pipe work, and container dikes are necessary. In addition, the activation system must be designed so that sufficient time is allowed for the NaBr and NaOCl solutions to fully react prior to being injected into the water being treated. Another disadvantage is that NaOCl solutions deteriorate rapidly, and so delivery pumps must continually be readjusted to compensate and ensure that the correct proportions of reactants are maintained for accurate dosing. This dual NaBr/NaOCl activation system is so cumbersome and difficult to control that many users have demanded a system in which the NaBr is supplied in a pre-activated, one-drum form that is stabilized to disproportionation and decomposition reactions. Clearly, a single feed liquid bromine biocide with these properties would be far more convenient and easier to use and control than the dual component approach.

One of the earlier attempts to develop a single feed, liquid bromine biocide is described in U.S. Pat. Nos. 4,886,915 and 4,966,716 to Favstritsky, et al. An aqueous solution containing 38% elemental bromine complexed as ethanolammonium hydrogen perbromide was administered to the water being treated. Subsequently, U.S. Pat. No. 5,141,652 taught the use of strong solutions of halide salts and hydrohalic acids to form solutions of bromine chloride complexes. However, neither technology became fully commercialized because the problem of bromine fuming from the products was not completely alleviated.

U.S. Pat. Nos. 5,683,654, 5,795,487, 5,942,126, and 6,136,205 describe processes to manufacture a single feed, liquid bromine biocide by mixing aqueous hypochlorite solutions with bromide ion sources and then stabilizing this reaction mixture to disproportionation and decomposition by introduction of a stabilizing agent. Although the resultant solutions did not evolve bromine fumes, the process required a complex two-step reaction. In the first step, NaBr and NaOCl solutions were mixed and sufficient time was allowed to permit the formation of a NaOBr solution. In the second step, this was then introduced to a solution of the stabilizing agent maintained at 50° C. However, the main limitation of this approach lay in the use of a NaOCl bleach solution as the foundation of the process. When NaOCl bleach was used as the activating agent, the concentration of the stabilized bromine product became limited by the concentration of NaOCl bleach that is commercially available. In fact, despite using the highest strength grades of industrial NaOCl bleach, the bromine content of the resulting stabilized solutions was only about 14% as $Br_2$ (6.3% as $Cl_2$).

Moore et al. overcame the complexity of the two-step reaction in U.S. Pat. Nos. 6,068,861, 6,495,169, and 6,322,822 and disclosed a single vessel reaction in which bromine or bromine chloride was added to a halogen stabilizer solution under conditions of pH control. The available bromine content of the resultant solutions was reported to be at least 10% as $Br_2$ (4.4% as $Cl_2$). However, when the process was scaled up, as disclosed in U.S. Pat. Nos. 6,299,909, 6,306,441, and 6,348,219, it was found necessary to employ a three-reactor sequence, and an upper limit of 18% as $Br_2$ (8% as $Cl_2$) was imposed as the highest strength concentrate that could be made by the process. Another drawback to the processes described by Moore et al. was the hazardous nature of the starting reagents involved. The high cost of transporting and handling of elemental bromine or bromine chloride meant that commercial manufacturing of the stabilized bromine solutions could only be accomplished in highly specialized, dedicated plants close to sites where bromine is recovered from naturally occurring brines. In the U.S., the process of Moore et al. could only be practiced economically in manufacturing plants close to the brine fields of southern Arkansas or Michigan.

Yang et al. sought to increase the concentration of the available bromine in the stabilized formulation, and disclosed processes in U.S. Pat. Nos. 6,156,229, 6,423,267, and 6,287,473 that also employed the use of elemental bromine, bromine chloride, or sodium bromate. Using these methods, liquid bromine concentrates containing 26.2% as $Br_2$ (11.6% as $Cl_2$) were prepared. However, it was reported that such solutions were physically Unstable, and large amounts of bromine-containing solids precipitated out of solution on standing overnight. Upon filtration of the solids, the liquid phase comprised 18.7% as $Br_2$ (8.3% as $Cl_2$). No information on the long-term chemical stability of the concentrates was reported. Other efforts to prepare stabilized liquid bromine formulations of high concentration were disclosed in U.S. Pat. No. 6,270,722 where high strength industrial grade sodium hypochlorite solutions and gaseous $Cl_2$ were used to oxidize sodium bromide solutions. Stabilized liquid bromine concentrates containing up to 20.75% as $Br_2$ (9.22% as $Cl_2$) were reported, but no information regarding the stability of the products to precipitation of solids was disclosed.

As is well noted in the prior art, the bromine content of stabilized formulations prepared using only sodium hypochlorite bleach solutions is limited by the strength of commercially available material. Indeed, even using the highest strength grade of industrial NaOCl bleach, the bromine content of the resulting solutions is reported to be only around 14% as $Br_2$ (6.3% as $Cl_2$). Although higher concentration solutions can be prepared with processes that employ $Br_2$, BrCl, or $Cl_2$, those processes result in a substantial amount of halide ion salt contaminants. Typically, when using these reagents, half of the respective Br atoms, and all of the respective chlorine atoms, materialize as halide ion salts. These halide ion salts are soluble and remain in the solution. These halide ion salts are deleterious because they: (1) limit the concentration of stabilized liquid bromine that can be attained in solution; (2) decrease the chemical stability of the resulting liquid bromine concentrates; and (3) decrease the physical stability of the liquid bromine concentrate resulting in undesirable precipitation of salts from solution.

Certainly, the physical and chemical stability of the liquid bromine solutions was of concern to McKinnie, et al. in U.S. Pat. No. 6,506,418. They reported that under the acidic conditions advocated in their earlier processes based on BrCl, $Br_2$, or $Cl_2$, "a substantial portion of the sulfamate can be hydrolyzed rather rapidly to sulfate" (col. 3, line 67 to col. 4, line 1) and further that "loss of sulfamate due to hydrolysis to sulfate can result in decreased storage stability of the finished product" (col. 4, line 3 to col. 4, line 5), later to point out that "loss of sulfamate imposes an economic burden on the operation" (col. 4, line 8 to col. 4, line 9). To overcome these deficiencies, acidic reaction conditions were discouraged, and alkaline pH conditions of 8-10 were recommended when introducing BrCl, $Br_2$, or $Cl_2$ to the reaction medium. Yang et al. also recognized the benefits of alkaline conditions in U.S. Pat. Nos. 6,123,870 and 6,287,473 for processes to prepare liquid bromine solutions. In these processes, BrCl or $Br_2$ was added to highly caustic solutions of sodium sulfamate such that the resulting solution had a pH of 12.5. It was claimed that without adequate pH control, rapid decomposition of the oxidizing species occurred.

Users of stabilized liquid bromine products recognize that formulations that contain higher levels of active ingredients have distinct economic advantages over dilute products since less product needs to be applied to a water system in order to achieve the equivalent dose of a weaker material. Also, more concentrated products need to be replaced less frequently than dilute products. Other advantages of concentrated liquids include reduced packaging, storage, and transportation costs per unit weight of active ingredient. Products prepared to contain high levels of dissolved active ingredients must display two essential attributes. First, they must be chemically stable, i.e. they should not decompose quickly, so as to maintain high activity for extended periods. Second, they must be physically stable, i.e. they should not precipitate or crystallize into solid salts that could plug pipe work and make the feeding of liquid materials grind to a halt.

Therefore, the need exists for liquid biocidal bromine compositions of higher concentration and superior physical and chemical stability than those described in the prior art and for methods of preparation of such compositions. There is a need for methods that employ inexpensive starting materials that are less hazardous and easier to handle than elemental liquid $Br_2$ or liquid BrCl. There is also a need for methods that are not restricted to manufacturing plants close to bromine recovery facilities and that may be conducted quickly and efficiently in a single reactor. This invention addresses these needs.

Additionally, there is a need for liquid biocidal compositions based on mixtures of bromine and chlorine. No such compositions have ever been reported. All of the prior efforts have been directed toward the preparation of compositions in which bromine is the sole active ingredient, primarily because of the superior biocidal performance of bromine compounds compared to chlorine compounds. In waters exerting a high halogen demand, however, it is more economical for the demand to be satisfied with lower cost chlorine chemistry than with higher cost bromine chemistry. Thus, there is a need for a liquid composition containing both bromine and chlorine. This invention addresses this need as well.

There is also a need for a solid high-activity bromine-containing biocidal composition that is stable and fast dissolving. There are several solid, high-activity bromine-releasing compounds that are sold commercially as biocidal products. They are generally available as heterocyclic organic compounds to which an oxidizing bromine atom is covalently bonded to a nitrogen atom on the ring. Examples include N,N' bromochloro-5,5-dimethylhydantoin, 1,3-dibromo-5,5-dimethylhydantoin, and mixtures of these compounds with various other components. In water, these materials hydrolyze to release hypobromous acid, which is the biocidal agent. However, the major limitation of these solid compounds is that they are only sparingly soluble in water. Indeed, N,N' bromochloro-5,5-dimethylhydantoin has a water solubility of only 0.1% at 20° C. As a result, bromine is only released very slowly from these products as they dissolve. This is a significant disadvantage when the water requires treatment with a high, rapid dose of biocidal bromine as is necessary in shock and slug dosing procedures. Therefore, there exists the need for solid, high-activity forms of bromine of high water solubility and which dissolve rapidly and completely to provide the water with a high, rapid dose of biocidal bromine. Additionally, these solid products must have a long shelf life and not lose activity prior to use. This invention addresses these needs.

SUMMARY OF THE INVENTION

The present invention is directed to methods of preparing highly concentrated liquid bromine-containing compositions and highly concentrated mixed halogen liquid bromine and chlorine-containing compositions, and high-activity solid bromine-containing compositions that have excellent physical and chemical stability. The invention is also directed to the compositions themselves.

The compositions of this invention are sources of oxidizing halogen that are useful for microbiological control in aqueous systems. This is generally achieved by introducing the compositions into water requiring microbiological control in an amount sufficient to be biocidally effective. Application areas include a number of industrial water systems such as recirculating cooling water, once-through cooling water, air washer systems, decorative fountains, oil field injection water, oil well completion fluids, municipal and industrial wastewater, brewery pasteurizing water, hydrostatic sterilizer cooling water, pulp and paper processing water, and agricultural irrigation water. Application areas also include a number of residential water systems where the home consumer can apply the compositions in aqueous systems where microbiological control is necessary. Some of these consist of pool and spa water, kitchen and bathroom rinses, toilet bowl rinses, and mold and fungus sprays for inside and outside the home.

The first, second, and third embodiments of the invention are methods for preparing liquid bromine-containing compositions. In the first embodiment, anhydrous hydrogen bromide gas and a concentrated solution of hydrogen peroxide are used to make a liquid composition. In the second embodiment, an aqueous solution of bromide ions, a concentrated solution of hydrogen peroxide, and a solid halogenating agent (either organic or inorganic) are used to make a liquid bromine-containing composition or a mixed halogen liquid bromine and chlorine-containing composition. In the third embodiment, an alkali metal or earth alkali metal solution of bromide ions is combined with a solid halogenating agent (either organic or inorganic) to make a liquid bromine-containing composition or a mixed halogen liquid bromine and chlorine-containing composition.

The fourth and fifth embodiments of the invention are methods for preparing solid bromine-containing compositions. The fourth embodiment utilizes a bromine compound in the oxidation state of −1, a concentrated solution of hydrogen peroxide, and a solid halogenating agent (either organic or inorganic). The fifth embodiment utilizes an alkali metal or earth alkali metal solution of bromide ions and an organic halogenating agent. Both the fourth and fifth embodiments may be used to prepare two end products. The first is a saturated solution of the alkali metal or earth alkali metal salt of hydrated N-bromosulfamate. The second is the solid alkali metal or earth alkali metal salt of hydrated (or anhydrous) N-bromosulfamate.

The sixth, seventh, and eighth embodiments of the invention are compositions of matter. The sixth embodiment is a highly concentrated bromine-containing liquid composition having an active ingredient content of at least about 18% as $Br_2$ (8% as $Cl_2$). This liquid has zero to about 1 mole of dissolved halide ion salts per mole of active halogen, depending on the method of preparation. Further, this liquid composition has physical stability in that it is not prone to solid precipitates and is stable to at least three cycles of freezing and thawing and has chemical stability in that its active ingredient half-life is at least about 58 days at 125° F. The liquid also has undetectable levels of bromate ion.

The seventh embodiment is a composition of matter, a highly concentrated mixed halogen liquid composition containing both bromine and chlorine, having an active ingredient content of at least about 11.25% as $Br_2$ (5% as $Cl_2$). It is characterized as containing less than about 1 mole of dissolved halide ion salts per mole of active halogen. Compared to the all-bromine composition of the sixth embodiment, the mixed halogen composition has even greater physical and chemical stability.

The eighth embodiment is two compositions of matter: the solid alkali metal or earth alkali metal salt of hydrated N-bromosulfamate and the solid alkali metal or earth alkali metal salt of anhydrous N-bromosulfamate. These high-activity solids are stable and dissolve quickly to yield a highly concentrated bromine-containing solution.

A significant advantage of this invention is that it provides stable, aqueous bromine-containing compositions that contain significantly lower amounts of contaminant halide ion salts than the methods of the prior art. The methods of the first and second embodiments result in liquid compositions that possess little or no halide ion salts because all or significantly all oxidation is accomplished with high strength hydrogen peroxide solutions. Contrary to processes that employ NaOCl/NaBr solutions, $Cl_2$/NaBr solutions, $Br_2$, or BrCl, hydrogen peroxide solutions contribute no inert ions or extraneous salts to the finished product that adversely impact its strength and stability. Thus, the methods of these embodiments minimize halide ion-induced physical and chemical destabilization. Assuming a 100% reaction yield, Table I compares the ratio of inactive, soluble halide ($X^-$) ion to active bromine that materializes with the product when various reagents are used.

TABLE I

| Reagent | Moles dissolved $X^-$ ion/mole stabilized active bromine |
|---|---|
| $Br_2$ | 1 |
| BrCl | 1 |
| NaOCl/NaBr | 2 |
| $Cl_2$/NaBr | 2 |
| Present invention | 0-0.8 |

Another notable advantage of this invention is that it makes possible the formation of highly concentrated liquid and high-activity solid bromine-containing compositions using inexpensive reagents. For example, the method of the first embodiment (yielding a liquid composition) and the method of the fourth embodiment (yielding a solid composition) may use anhydrous hydrogen bromide gas. This gas is a by-product of chemical reactions in which organic compounds are brominated with elemental $Br_2$. Gaseous anhydrous hydrogen bromide escapes the reactor and is normally scrubbed into water to form a solution of 48%-70% aqueous hydrogen bromide solution that is either piped to a separate unit operation for production of more elemental $Br_2$, or is neutralized and disposed of as waste. The methods of the first, second, and fourth embodiments also use an inexpensive oxidizing agent, hydrogen peroxide.

A major benefit of the methods of the second, third, fourth, and fifth embodiments is that they use solid halogenating agents. Because solid halogenating agents are devoid of water, the bromine content of the finished compositions is not diluted as it is where hypochlorite solutions are used. Further, these solid halogenating agents are generally high in available halogen and do not contain large amounts of extraneous salts or inactive ingredients that enter the finished product. Hence, the compositions that are obtained using solid halogenating agents possess lower levels of water, as well as lower levels of dissolved salts or other extraneous materials, which would otherwise dilute the available bromine content of the product and adversely impact its chemical and physical stability.

Another remarkable benefit of this invention is that the methods of the second and third embodiments make possible the formation of highly concentrated liquid bromine-containing compositions employing processes that generate no solid wastes. Thus, using solid organic halogenating reagents such as trichloroisocyanuric acid (TCCA) (also known as trichloro-s-triazinetrione), sodium dichlorisocyanurate (NaDCC) (also known as sodium dichloro-s-triazinetrione), or sodium dichlorisocyanurate dihydrate (NaDCC.$2H_2O$) (also known as sodium dichloro-s-triazinetrione dihydrate), the by-product of the halogenation reaction is cyanuric acid (CA). This is insoluble in the reaction medium and precipitates in a solid form. Upon filtration and washing, highly purified CA wetcake is recovered. This can be recycled to other processes to make additional quantities of TCCA, NaDCC or NaDCC.2H$_2$O that can be used in the method of the current invention.

A further benefit of the method of the third embodiment of the invention is that it results in a liquid mixed halogen bromine and chlorine-containing composition that is safer and more convenient to produce than those that are predominantly bromine based.

A very surprising discovery of the invention is that the methods of the second and third embodiments use solid halogenating agents, instead of the liquid precursors used in the prior art, to prepare liquid bromine-containing compositions. The prior art methods use NaOCl solutions, Br$_2$, or BrCl and describe chemistries that are designed to be accomplished under homogeneous, liquid phase conditions. The second and third embodiments are not performed under such conditions. Rather, they are performed under distinctly different, heterogeneous, solid-liquid conditions, because the solid halogenating agents never completely dissolve. The reaction chemistries of the second and third embodiments proceed rapidly, smoothly, and in high yield.

A further very surprising discovery of the present invention is that, using the method of the second embodiment, highly concentrated liquid bromine-containing compositions can be prepared under conditions of extremely high acidity. Indeed, the prior art teaches that such conditions are to be avoided in order to suppress undesirable hydrolysis of the sulfamic acid to ammonium sulfate. The presence of sulfate is undesirable because it is prone to precipitate and impair the physical stability of the solution. The presence of ammonium ion is undesirable as it reacts destructively with halogens to reduce the chemical yield of the reaction resulting in the formation of troublesome nitrogen gas bubbles in the reactor.

It is a further very surprising discovery of the present invention that the methods of the second and third embodiments use solid, organic halogenating agents instead of a NaOCl solutions, Br$_2$, or BrCl to prepare aqueous bromine-containing compositions of far higher concentrations than previously reported. This is because solid, organic halogenating agents typically display only very limited water solubility, so it would be expected that the maximum concentration of a halogen-containing composition prepared using such materials would be correspondingly low. For example, trichloroisocyanuric acid dissolves in water to yield a saturated solution of just 1.1% as Cl$_2$ at 25° C. Nevertheless, the method of the present invention uses trichloroisocyanuric acid to prepare aqueous bromine-containing compositions having levels of halogen equivalent to almost 11% as Cl$_2$.

Another advantage of this invention is that the fourth and fifth embodiments make possible the formation of a highly soluble bromine-containing solid composition using reagents that are more convenient to handle and less expensive to transport than alkali metal or earth alkali metal hypochlorite solutions.

The invention also has the advantage of using a single reactor sequence. In the methods of all of the embodiments, the complexing agent is introduced to the reaction as the free acid without the requisite for preforming its alkali metal or earth alkali metal salt in a separate reactor. Accordingly, since highly acidic conditions are maintained throughout the oxidation reactions, the possibility of bromate ion (an undesirable, carcinogenic by-product) being formed within the composition is eliminated.

Still another feature of the invention is that the fourth and fifth embodiments make possible the manufacture of a highly soluble bromine-containing solid composition in a process that neither employs nor generates measurable amounts of bromate.

Another advantage of this invention is that the methods of all of the embodiments make possible the formation of highly concentrated liquid or high-activity solid bromine-containing compositions in a series of fast, efficient, and high-yielding reactions.

This invention is also advantageous in that the methods of all of the embodiments make possible the formation of highly concentrated liquid or high-activity solid bromine-containing compositions using reagents that are safer, easier, and more convenient to handle and transport than the hazardous materials BrCl, elemental Br$_2$, or gaseous Cl$_2$ utilized in the prior art processes.

DETAILED DESCRIPTION OF THE INVENTION

The First Embodiment

This embodiment is a method of preparing a highly concentrated aqueous bromine-containing biocide composition using anhydrous hydrogen bromide gas and a concentrated solution of hydrogen peroxide. The method preferably includes the following steps. Steps (a) and (b) may be performed in any order, or simultaneously, followed by step (c).

a. Mixing a complexing agent with a concentrated solution of hydrogen peroxide to form a slurry.

Preferably, the complexing agent is solid sulfamic acid and is introduced to the hydrogen peroxide solution with stirring. Hydrogen peroxide solution is commercially available at concentrations up to 90%, but 50% hydrogen peroxide is recommended as it is safer to use and is more commonly available.

b. Introducing a source of covalently bonded anhydrous hydrogen bromide gas into the slurry.

One source of anhydrous hydrogen bromide gas is the reaction medium in which bromide ion is released from an organobromine complex in a nucleophilic displacement reaction. An example would be the reaction of methyl bromide with sodium hydroxide (reaction 1) followed by acidification with mineral acid (reaction 2):

$$CH_3\text{—}Br+NaOH \rightarrow CH_3\text{—}OH+NaBr \qquad (1)$$

$$NaBr+HCl \rightarrow NaCl+HBr(g) \qquad (2)$$

However, a preferred source of anhydrous hydrogen bromide gas is an emission from a reactor where bromination of an organic compound is taking place.

$$R\text{—}H+Br_2 \rightarrow R\text{—}Br+HBr(g) \qquad (3)$$

The hydrogen bromide gas is directed subsurface, and with agitation, to a reactor containing the slurry of sulfamic acid in strong hydrogen peroxide solution. The hydrogen peroxide oxidizes the hydrogen bromide gas to bromine as shown in reaction (4). Bromine reacts with sulfamic acid to form a bromo derivative and co-produce an additional amount of hydrogen bromide as illustrated by reaction (5).

$$2HBr+H_2O_2 \rightarrow Br_2+2H_2O \qquad (4)$$

$$Br_2+NH_2\text{—}SO_3H \rightarrow [Br][NH\text{—}SO_3H]+HBr \qquad (5)$$

Recycle in (4)

The amount of anhydrous hydrogen bromide gas added to the reactor is such that between 10% and 100% of the Br moieties form a complex with sulfamic acid. The amount of sulfamic acid present in the slurry depends on the amount of anhydrous hydrogen bromide introduced to the reactor. A mole ratio of about 0.75:1 to about 1.5:1 sulfamic acid:hydrogen bromide is advantageous to the stability of the final product with about 0.95:1 to about 1.2:1 being the most preferred mole ratio range.

The reaction time and temperature are controlled in order to maximize the conversion of hydrogen bromide gas into bromine, and minimize the amount of unreacted hydrogen peroxide remaining in the reaction medium. Processing can be performed in the batch or continuous mode. In continuous processing, the reactor size can be significantly reduced without loss in product output rate. The reactants are co-fed to a common junction as the reaction products are continuously withdrawn. In both continuous and batch processes, the reactions are conducted with mixing. The oxidation of hydrogen bromide gas with hydrogen peroxide is an exothermic reaction. Heat removal is effected by conducting the reaction at the refluxing temperature of the reaction mixture using a condenser to facilitate the heat removal process. Alternatively, cooling is effected with a jacketed reactor.

When hydrogen peroxide is used in this fashion, all of the Br moieties introduced to the reactor as hydrogen bromide materialize as active bromine in the final product. None are wasted as by-product bromide ion salts.

c. Adding an alkaline source to the reaction medium.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used in the process of this invention. The sodium hydroxide solution is introduced to the reaction medium slowly, and with stirring and cooling such that the temperature does not exceed 80° F. The purpose is to deprotonate the bromo derivative of sulfamic acid to form the bromo derivative of sodium sulfamate according to reaction (6).

[Br][NH—SO$_3$H]+NaOH→[Br][NH—SO$_3^-$][Na$^+$]+ H$_2$O    (6)

The amount of NaOH solution employed depends on its strength and on the initial charge of hydrogen bromide gas. The overall mole ratio of hydrogen bromide gas to NaOH is in the range of about 1:2 to about 1:5 and preferably about 1:3 to about 1:4.

PROSPECTIVE EXAMPLE 1

Hydrogen bromide gas (8.09 g/min) is directed to a mixing unit for contact with a slurry formed by combining sulfamic acid (11.64 g/min) and 50% hydrogen peroxide (6.8 g/min). The overall reaction is:

H$_2$O$_2$+NH$_2$—SO$_3$H+HBr→[Br][NH—SO$_3$H]+2H$_2$O    (7)

The temperature and contact time are controlled so that the reaction is driven to completion and no unreacted H$_2$O$_2$ remains in the reaction medium whereupon 50% NaOH (28.0 g/min) is introduced to complete the process according to reaction (8).

[Br][NH—SO$_3$H]+NaOH→[Br][NH—SO$_3^-$][Na$^+$]+ H$_2$O    (8)

The Second Embodiment

This embodiment is a method of preparing highly concentrated liquid bromine-containing compositions using an aqueous solution of bromide ions, a concentrated solution of hydrogen peroxide, and a solid halogenating agent (either organic or inorganic).

Overall, this method is advantageous in that it uses a high strength hydrogen peroxide solution in combination with a solid halogenating agent. This method results in a composition that contains significantly lower amounts of contaminant halide ion salts than solutions prepared using Br$_2$, BrCl, Cl$_2$/NaBr, or NaOCl/NaBr solutions and is thus highly stable to chemical and physical decomposition processes. This stabilized composition possesses far higher bromine concentrations than those available from using Br$_2$, BrCl, Cl$_2$, and even the strongest solutions of sodium hypochlorite. Thus, practice of this method provides a stable, aqueous composition of matter that contains 60-80% more available bromine than solutions that are currently commercially available. Moreover, the aqueous composition of this invention contains the highest concentration of bromine hitherto reported in the prior art. Typically, the composition of this invention contains greater than 21.4% as Br$_2$ (9.4% as Cl$_2$). It is golden yellow in color.

The method of this embodiment may also be used to prepare a liquid mixed halogen composition that contains both bromine and chlorine. The method uses a solution of bromide ions in conjunction with a molar excess of the combination of hydrogen peroxide and a solid chlorinating agent (either organic or inorganic). This light golden-colored composition contains 60-80% more available halogen than the all-bromine solutions that are currently available commercially. Typically, the mixed halogen composition prepared using this method contains a total halogen level of greater than 21% expressed as Br$_2$ (9.4% expressed as Cl$_2$).

A major benefit of a mixed halogen biocide is in the treatment of contaminated water that exerts a considerable halogen demand. This chemical demand can be satisfied by the less expensive chlorine portion of the composition, permitting more of the bromine portion to be available for microbiological control. Mixed halogen compositions are also safer and more convenient to manufacture than those that are predominantly bromine based. For example, during the preparation of the latter, the solutions have a tendency to emit deep red, highly corrosive and toxic bromine fumes right up until the final addition of the alkaline source. These vapors must be scrubbed from the reaction vessel's headspace in order to eliminate atmospheric release, worker exposure, and to prevent the fumes from entering and damaging expensive vacuum processing equipment. By contrast, the mixed halogen compositions emit hardly any deep red bromine fumes during their manufacture. Thus, the necessity for scrubbing the reaction vessel's headspace is eliminated.

A further significant aspect of compositions based on mixtures of stabilized bromine and chlorine is that in water systems employing long contact times, there may be sufficient time for the N-chlorosulfamate to react with "spent" bromide ion and regenerate N-bromosulfamate according to the following schematic.

[Br—NH—SO$_3^-$]+H$_2$O=HOBr+NH$_2$SO$_3^-$

Upon performing biocidal and oxidative reactions, HOBr reverts to soluble bromide ion. This can enter into reaction with N-chlorosulfamate to form additional N-bromosulfamate:

[Cl—NH—SO$_3^-$]+Br$^-$=[Br—NH—SO$_3^-$]+Cl$^-$

In this way, the consumer is able to derive the performance benefits of 2 moles of N-bromosulfamate for the price of 1 mole of N-bromosulfamate and 1 mole of N-chlorosulfamate.

As a general rule, chlorinated compounds display higher water solubility than their brominated counterparts. Further, a mixed halogen composition may be formulated to employ far less sodium bromide salt than an all-bromine solution. Thus, another highly advantageous facet of this invention is that it makes possible the formation of a mixed halogen composition that is lower in solids and is inherently more soluble than those based solely on bromine. This highly water-soluble composition exhibits improved physical stability as it becomes less prone to solid precipitation on storage.

1. The Method of Preparing an all-Bromine Composition Using Hydrogen Peroxide The method preferably includes the following steps. Steps (a), (b), and (c) may be performed in any order, or simultaneously, followed by step (d).

a. Utilizing an aqueous solution of bromide ions in which the pH is less than +1.

The first step of this method is conducted under conditions of extreme acidity, preferably at a pH which is greater than −1 and less than +1. Any acidified source of bromide ions can be employed in the practice of this invention, for example, an aqueous solution of sodium bromide acidified with a strong mineral acid such as hydrochloric or nitric acid. However, aqueous hydrogen bromide is a preferred starting material and can be used at any concentration up to 70% by weight, although 48% is especially convenient to use as this is the concentration at which the product does not appreciably fume HBr vapors.

b. Introducing to the highly acidic solution of bromide ions, a highly concentrated solution of hydrogen peroxide to effect a partial or complete oxidation of the bromide ions into bromine.

$$2HBr(aq) + H_2O_2 \rightarrow Br_2 + 2H_2O \quad (9)$$

Strong solutions of hydrogen peroxide are preferably introduced to the 48% aqueous hydrogen bromide solution, although the order of addition can be changed without appreciably effecting the reaction. Hydrogen peroxide is commercially available at concentrations up to 90%, but 50% hydrogen peroxide is safer to use and is more commonly available. Preferably, 50% hydrogen peroxide is added slowly and with stirring to a solution of 48% aqueous hydrogen bromide calculated to have a pH of −0.78. The amount of 50% hydrogen peroxide added to the 48% aqueous hydrogen bromide solution should be sufficient to oxidize between 10% and 100% of the stoichiometric amount and, most preferably, between 20% and 80% of the stoichiometric amount of bromide ions into bromine. The oxidation of aqueous hydrogen bromide with hydrogen peroxide is an exothermic reaction. Heat removal is effected by conducting the reaction at the refluxing temperature of the reaction medium using a condenser to facilitate the heat removal process. Alternatively, cooling is effected with a jacketed reactor. The reaction time and temperature are controlled in order to maximize the conversion of bromide into bromine and minimize the amount of unreacted hydrogen peroxide remaining in the reaction medium.

When hydrogen peroxide is used in this fashion, all of the Br moieties introduced to the reactor as hydrobromic acid can materialize as active bromine in the final product. None are wasted as by-product bromide ion salts. In this regard, hydrogen peroxide may also be used advantageously in reactions where elemental bromine is the starting raw material. Instead of wasting half of the Br moieties as inactive bromide ion, regeneration by hydrogen peroxide as described in reactions (9) and (10) will ensure that both bromine atoms are utilized as active forms.

c. Mixing a complexing agent to the fully or partially oxidized solution.

On allowing the highly acidic, bromine-laden reaction mixture to cool, a complexing agent is introduced to the same reactor. Preferably the complexing agent is solid sulfamic acid. Bromine reacts with sulfamic acid to form a bromo-derivative and co-produces an additional amount of hydrogen bromide as illustrated by reaction (10).

$$Br_2 + NH_2-SO_3H \rightarrow [Br][NH-SO_3H] + HBr \quad (10)$$

The amount of sulfamic acid added depends on the amount of aqueous hydrogen bromide originally present. A mole ratio of about 0.75:1 to about 1.5:1 sulfamic acid to aqueous hydrogen bromide is advantageous to the stability of the final product, with about 0.95:1 to about 1.2:1 being the most preferred mole ratio range.

In the event that the reaction medium is 100% oxidized by hydrogen peroxide in step (b), the method concludes with step (d). However, even in the event that the reaction medium is only partially oxidized in step (b), the method concludes with step (d).

d. Adding an alkaline source to the reaction mother liquors such that if the alkaline source is a hydroxide salt, the overall mole ratio of aqueous hydrogen bromide to hydroxide is between about 1:2 and about 1:5, preferably between about 1:3 and about 1:4.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F. The purpose is to deprotonate the bromo derivative of sulfamic acid to form the bromo derivative of sodium sulfamate according to reaction (14).

$$[Br][NH-SO_3H] + NaOH \rightarrow [Br][NH-SO_3^-][Na^+] + H_2O \quad (11)$$

The amount of 50% NaOH solution employed depends on the initial charge of aqueous hydrogen bromide. The overall mole ratio of aqueous hydrogen bromide to NaOH added in steps (d) is in the range of about 1:2 and about 1:5, preferably about 1:3 to about 1:4.

2. The Method of Preparing an All-Bromine Composition Using Hydrogen Peroxide and a Solid Organic Halogenating Agent The method preferably includes the following steps. Steps (a), (b), and (c) may be performed in any order, or simultaneously, followed by the remaining steps.

a. Utilizing an aqueous solution of bromide ions in which the pH is less than +1.

The first step of this method is conducted under conditions of extreme acidity, preferably at a pH which is greater than −1 and less than +1. Any acidified source of bromide ions can be employed in the practice of this invention, for example, an aqueous solution of sodium bromide acidified with a strong mineral acid such as hydrochloric or nitric acid. However, aqueous hydrogen bromide is a preferred starting material and can be used at any concentration up to 70% by weight, although 48% is especially convenient to use as this is the concentration at which the product does not appreciably fume HBr vapors.

b. Introducing to the highly acidic solution of bromide ions, a highly concentrated solution of hydrogen peroxide to effect a partial or complete oxidation of the bromide ions into bromine.

$$2HBr(aq) + H_2O_2 \rightarrow Br_2 + 2H_2O \qquad (12)$$

Strong solutions of hydrogen peroxide are preferably introduced to the 48% aqueous hydrogen bromide solution, although the order of addition can be changed without appreciably effecting the reaction. Hydrogen peroxide is commercially available at concentrations up to 90%, but 50% hydrogen peroxide is safer to use and is more commonly available. Preferably, 50% hydrogen peroxide is added slowly and with stirring to a solution of 48% aqueous hydrogen bromide calculated to have a pH of –0.78. The amount of 50% hydrogen peroxide added to the 48% aqueous hydrogen bromide solution should be sufficient to oxidize between 10% and 100% of the stoichiometric amount and, most preferably, between 20% and 80% of the stoichiometric amount of bromide ions into bromine. The oxidation of aqueous hydrogen bromide with hydrogen peroxide is an exothermic reaction. Heat removal is effected by conducting the reaction at the refluxing temperature of the reaction medium using a condenser to facilitate the heat removal process. Alternatively, cooling is effected with a jacketed reactor. The reaction time and temperature are controlled in order to maximize the conversion of bromide into bromine and minimize the amount of unreacted hydrogen peroxide remaining in the reaction medium.

c. Mixing a complexing agent to the fully or partially oxidized solution.

On allowing the highly acidic, bromine-laden reaction mixture to cool, a complexing agent is introduced to the same reactor. Preferably the complexing agent is solid sulfamic acid. Bromine reacts with sulfamic acid to form a bromo-derivative and co-produces an additional amount of hydrogen bromide as illustrated by reaction (13).

$$Br_2 + NH_2\text{---}SO_3H \rightarrow [Br][NH\text{---}SO_3H] + HBr \qquad (13)$$

The amount of sulfamic acid added depends on the amount of aqueous hydrogen bromide originally present. A mole ratio of about 0.75:1 to about 1.5:1 sulfamic acid to aqueous hydrogen bromide is advantageous to the stability of the final product, with about 0.95:1 to about 1.2:1 being the most preferred mole ratio range.

d. Adding an alkaline source to the reaction medium to adjust its pH to between about 0.5 and about 9 and preferably between about 1.0 and about 4.5.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F. The purpose is to deprotonate the bromo derivative of sulfamic acid to form the bromo derivative of sodium sulfamate according to reaction (14).

$$[Br][NH\text{---}SO_3H] + NaOH \rightarrow [Br][NH\text{---}SO_3^-][Na^+] + H_2O \qquad (14)$$

e. Introducing sufficient solid, organic halogenating agent to oxidize all or substantially all of the remaining bromide ions into bromine.

Solid organic halogenating agents include any organic compound in which one or more halogen atoms such as Cl, Br, or I is present in oxidation state +1 and is covalently bound to a nitrogen or phosphorus atom within the same molecule. Suitable examples include, but are not limited to, trichloroisocyanuric acid (TCCA), sodium dichloroisocyanurate (NaDCC), sodium dichloroisocyanurate dihydrate (NaDCC.2H$_2$O), potassium dichloroisocyanurate (KDCC), dichloroisocyanuric acid (DCCA), trichloromelamine, N-chloro-p-toluenesulfonamide, N-chloromethanesulfonamide, N-chlorosuccinimide, N,N'-1,3-bromochloro-5,5-dimethylhydantoin, N,N'-1,3-bromochloro-5-ethyl-5-methylhydantoin, 1,3-dibromo-5,5-dimethylhydantoin, 1,3-dichloro-5,5-dimethylhydantoin, and N-bromosuccinimide. A particularly preferred source of a solid, organic halogenating agent is trichloroisocyanuric acid (TCCA), which reacts with aqueous hydrogen bromide and unreacted sulfamic acid according to the following equation.

$$NH_2\text{---}SO_3H + HBr + TCCA \rightarrow [Br][NH\text{---}SO_3H] + Cl^- + \text{Cyanuric acid} \qquad (15)$$

Preferably TCCA is used in the form of a coarse granular grade of material for ease of introduction to the stirred, cooled reactor. As the TCCA reacts, the coarse granules disappear. The reaction is considered to be complete when no more coarse granules are evident. Although granular TCCA is favored because of its easy handling characteristics, and for providing a visual signal that the reaction is complete, TCCA powdered wetcake may also be employed. The advantage of using TCCA powdered wetcake is that it may be taken directly from the TCCA-producing reactors to eliminate costs associated with drying and granulation of the material.

f. Removing any insoluble reaction by-products with a conventional solid-liquid separation technique.

Any suitable solid-liquid separation technique can be employed. Suitable examples include, but are not limited to, centrifugation, clarification, gravity sedimentation, and vacuum filtration. Filtration is a particularly preferred technique for effecting solid-liquid separation. When the solid organic halogenating agent is TCCA, cyanuric acid (CA) is a reaction by-product that is insoluble in the reaction medium (see reaction (15)). Filtration of the CA residue is carried out at pH 1-9, but preferably at pH 1.5-4.5 to maximize its recovery from solution and minimize the amount of bromine vapor that fumes from the reaction medium. Upon washing the filtercake with water to remove the mother liquors, a highly pure CA wetcake is recovered. This can be recycled to other processes in order to make additional quantities of TCCA, NaDCC, or NaDCC.2H$_2$O that can be used in the method of the current invention.

If desired, this step can be modified so that the sodium salt of cyanuric acid is recovered from the reaction medium instead of cyanuric acid. This is accomplished by introducing, before performing the solid-liquid separation, sufficient 50% NaOH to react with cyanuric acid according to the following equation:

$$CA + NaOH \rightarrow NaCA + H_2O \qquad (16)$$

The amount of 50% sodium hydroxide solution employed depends on the amount of solid organic halogenating agent used in step (e) that is introduced to oxidize all or substantially all of the remaining bromide ions into bromine. When TCCA is the solid organic halogenating agent, sufficient 50% NaOH solution is introduced slowly with mixing and cooling to convert all or substantially all of the cyanuric acid liberated in equation (15) into its monosodium salt via reaction (16). Monosodium cyanurate is insoluble in the reaction medium at pH<9. As is true of cyanuric acid, monosodium cyanurate can be separated and recycled to other processes in order to make additional quantities of TCCA, NaDCC, or NaDCC.2H$_2$O that can be used in the method of the current invention. This is accomplished by performing a solid-liquid separation, as described above, which is done when the pH stabilizes at about 9.

g. Adding an alkaline source to the reaction mother liquors such that if the alkaline source is a hydroxide salt, the overall mole ratio of aqueous hydrogen bromide to hydroxide is between about 1:2 and about 1:5, preferably between about 1:3 and about 1:4. This does not include any hydroxide salt that may be used to convert cyanuric acid into its alkali metal or earth alkali metal salt as described in step (f).

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F. The purpose is to deprotonate the bromo derivative of sulfamic acid to form the bromo derivative of sodium sulfamate according to reaction (17).

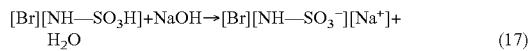

[Br][NH—SO$_3$H]+NaOH→[Br][NH—SO$_3^-$][Na$^+$]+ H$_2$O　　(17)

The amount of 50% NaOH solution employed depends on the initial charge of aqueous hydrogen bromide. The overall mole ratio of aqueous hydrogen bromide to NaOH added in steps (d) and (g) is in the range of about 1:2 and about 1:5, preferably about 1:3 to about 1:4. This does not include any 50% NaOH solution that may be used to convert cyanuric acid into its monosodium salt as described in step (f).

h. Removing any further insoluble residues that develop with a conventional solid-liquid separation technique.

As noted above, any suitable solid-liquid separation technique may be employed. Generally, when TCCA is the halogenating agent, almost 90% of CA reaction by-product is recovered as a highly pure wetcake in the first solid-liquid separation step described in step (f). While not wishing to be bound by theory, it is believed that salts of cyanuric acid are precipitated from the reaction mother liquors upon the addition of alkaline sources. When the alkaline source is, for example, 50% sodium hydroxide solution, the mono-, di-, and trisodium salts of cyanuric acid are precipitated. Although insoluble in the reaction mother liquors, the di and trisodium salts display exceptional solubility in ordinary water and are thus useful water treating agents in their own right. However, in comparison to the amount of solids recovered in step (f), the amount of solid that may subsequently develop is relatively low and step (h) may require only a polishing solid-liquid separation, with, for example, a cartridge filter. Moreover, the two solid-liquid separation steps of (f) and (h) may be combined into a single operation performed only at step (f).

Examples 2-8

A general procedure for preparing the liquid stabilized bromine concentrates listed in Table II is as follows:

To a stirred reaction flask containing 48% hydrogen bromide (27.8 g) was added 50% H$_2$O$_2$ (4.26 g) dropwise so that the reaction flask temperature did not exceed 142° F. After allowing the reaction flask to cool to around 95° F., solid sulfamic acid (19.2 g) was introduced. The resulting slurry was stirred as 50% sodium hydroxide solution was charged to the reaction flask to give a pH of between 1 and 10. The flask was chilled during this process so that the temperature did not exceed 80-90° F. A single charge of granular trichloroisocyanuric acid (8.81 g) was introduced to the reaction flask and stirred for 10-15 minutes or until all the coarse granules were observed to have reacted and a fine powdery precipitate developed. The solid was removed by vacuum filtration and the filter cake was washed with deionized water that was combined with the mother liquors. A second charge of 50% NaOH was then introduced also with cooling, and stirring at a rate such that the temperature did not exceed 80-90° F. Any additional precipitate that developed was immediately removed by vacuum filtration or the reaction flask was allowed to stand overnight and then filtered. In each case, the filter cake was washed with deionized water that was combined with the mother liquors. Iodometric titration of the resulting golden yellow solutions was used to determine the weight % Br$_2$ (or Cl$_2$) contents. The theoretical amounts of Br$_2$ (or Cl$_2$ equivalent) produced as a function of the sum of the hydrogen peroxide and TCCA charges were then used to compute the % yield of each reaction.

TABLE II

| Example | Initial 50% NaOH charge/g | pH before TCCA addition | Second 50% NaOH charge/g | Amount D.I. wash water to mother liquors | Final pH | Wt % as Br$_2$ (Cl$_2$) | % Yield |
|---|---|---|---|---|---|---|---|
| 2 | 22.0 | NM | 15.75 | 2 × 5 ml | 12.4 | 23.5 (10.45) | 87.0 |
| 3 | 22.0 | 1.5 | 14.95 | 1 × 5 ml | 12.9 | 22.9 (10.2) | 80.1 |
| 4 | 22.0 | NM | 31.2 | 2 × 5 ml | 12.6 | 22.05 (9.8) | 93.7 |
| 5 | 25.0 | 10.4* | 20.0 | 2 × 5 ml | >12.5 | 24.36 (10.83) | 96.5 |
| 6 | 22.4 | 3.3 | 20.5 | 1 × 5 ml | 13.25 | 23.32 (9.92) | 82.7 |

TABLE II-continued

| Example | Initial 50% NaOH charge/g | pH before TCCA addition | Second 50% NaOH charge/g | Amount D.I. wash water to mother liquors | Final pH | Wt % as Br$_2$ (Cl$_2$) | % Yield |
|---|---|---|---|---|---|---|---|
| 7 | 20.4 | NM | 25.0 | 1 × 5 ml + 1 × 2 ml | 13.0 | 22.36 (9.94) | 86.5 |
| 8# | 20.5 | NM | 24.0 | 2 × 5 ml | 12.93 | 21.96 (9.76) | 88.4 |

*prior to TCCA addition, the pH was readjusted to 2.4 by addition of a little sulfamic acid.
the TCCA was substituted with 14.5 g sodium dichloroisocyanurate dihydrate (NaDCC.2H$_2$O) in this example.
NM denotes a parameter that was not measured.

Example 9

This example represents a four-fold scale-up of the reactions described in examples 2-8.

To a stirred reaction flask containing 48% hydrogen bromide (111.2 g) was added 50% H$_2$O$_2$ (16.96 g) dropwise so that the reaction flask temperature did not exceed 142° F. After allowing the reaction flask to cool to around 85° F., solid sulfamic acid (76.8 g) was introduced. The resulting slurry was stirred as 50% sodium hydroxide solution (91.9 g) was charged to the reaction flask to give a pH of 1.5. The flask was chilled during this process so that the temperature did not exceed 80-90° F. A single charge of granular trichloroisocyanuric acid (TCCA) (36.0 g) was introduced to the reaction flask that was stirred for 20 minutes. Most of the coarse TCCA granules were observed to have reacted within this period, as a fine powdery precipitate developed and the pH of the reaction medium was measured to be 1.5. Deionized water (28 g) was added to the reaction flask to facilitate the complete reaction of the TCCA. The cyanuric acid solid was removed by vacuum filtration and the filter cake was washed with deionized water (12.5 ml) that was not combined with the mother liquors. The wet filter cake was placed in an oven at 130° F. for drying overnight. To the filtration mother liquors was added 50% NaOH (104 g), also with cooling, and at a rate such that the temperature did not exceed 80-90° F. Any additional solid cyanurate salts that developed were removed by vacuum filtration. The solids retained on the filter were washed with deionized water (5.0 g) and then dried in an oven at 130° F. Iodometric titration of the resultant golden yellow solution yielded a % Br$_2$ content of 23.7% (or 10.54% as Cl$_2$). The theoretical amount of Br$_2$ (or Cl$_2$ equivalent) produced as a function of the sum of the hydrogen peroxide and TCCA charges was used to compute a reaction yield of 93.6%. The weight of the dried solids removed by filtration indicated that cyanuric acid and cyanurate salts were recovered in close to quantitative yield.

3. The Method of Preparing an all-Bromine Composition Using Hydrogen Peroxide and a Solid Inorganic Halogenating Agent The method preferably includes the following steps. Steps (a), (b), and (c) may be performed in any order, or simultaneously, followed by the remaining steps.

a. Utilizing an aqueous solution of bromide ions in which the pH is less than +1.

The first step of this method is conducted under conditions of extreme acidity, preferably at a pH which is greater than −1 and less than +1. Any acidified source of bromide ions can be employed in the practice of this invention, for example, an aqueous solution of sodium bromide acidified with a strong mineral acid such as hydrochloric or nitric acid. However, aqueous hydrogen bromide is a preferred starting material and can be used at any concentration up to about 70% by weight, although 48% is especially convenient to use, as this is the concentration at which the product does not appreciably fume HBr vapors.

b. Introducing to the highly acidic solution of bromide ions, a highly concentrated solution of hydrogen peroxide to effect a partial or complete oxidation of the bromide ions into bromine.

$$2HBr(aq) + H_2O_2 \rightarrow Br_2 + 2H_2O \qquad (18)$$

Strong solutions of hydrogen peroxide are preferably introduced to the 48% aqueous hydrogen bromide solution, although the order of addition can be changed without appreciably effecting the reaction. Hydrogen peroxide is commercially available at concentrations up to 90%, but 50% hydrogen peroxide is safer to use and is more commonly available. Preferably, 50% hydrogen peroxide is added slowly and with agitation to a solution of 48% aqueous hydrogen bromide which has a pH −0.78. The amount of 50% hydrogen peroxide added to the 48% aqueous hydrogen bromide solution should be sufficient to oxidize between 10% and 100% of the stoichiometric amount, and most preferably between 20% and 80% of the stoichiometric amount of bromide ions into bromine. The oxidation of aqueous hydrogen bromide with hydrogen peroxide is an exothermic reaction. Heat removal is effected by conducting the reaction at the refluxing temperature of the reaction mixture using a condenser to facilitate the heat removal process. Alternatively, cooling is effected with a jacketed reactor. The reaction time and temperature are controlled in order to maximize the conversion of bromide into bromine and minimize the amount of unreacted hydrogen peroxide remaining in the reaction medium.

c. Mixing a complexing agent to the fully or partially oxidized solution.

On allowing the highly acidic, bromine-laden reaction mixture to cool, a complexing agent is introduced to the same reactor. Preferably the complexing agent is solid sulfamic acid. Bromine reacts with sulfamic acid to form a bromo-derivative and co-produces an additional amount of hydrogen bromide as illustrated by reaction (19).

$$Br_2 + NH_2-SO_3H \rightarrow [Br][NH-SO_3H] + HBr \qquad (19)$$

The amount of sulfamic acid added depends on the amount of aqueous hydrogen bromide originally present. A mole ratio of about 0.75:1 to about 1.5:1 sulfamic acid to aqueous hydrogen bromide is advantageous to the stability of the final product, with about 0.95:1 to about 1.2:1 being the most preferred mole ratio range.

d. Adding an alkaline source to the reaction mother liquors such that if the alkaline source is a hydroxide salt, the overall mole ratio of aqueous hydrogen bromide to hydroxide is between about 0.5:1 and about 1:2, preferably between about 1:1.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F. The purpose is to deprotonate the bromo derivative of sulfamic acid to form the bromo derivative of sodium sulfamate according to reaction (20).

$$[Br][NH-SO_3H] + NaOH \rightarrow [Br][NH-SO_3^-][Na^+] + H_2O \qquad (20)$$

e. Introducing sufficient solid, inorganic halogenating agent to oxidize all or substantially all of the remaining bromide ions into bromine.

Solid inorganic halogenating agents include, but are not limited to, alkali metal and earth alkali metal hypochlorite salts. Suitable examples include lithium hypochlorite, calcium hypochlorite, and magnesium hypochlorite. Due to its low cost and high available chlorine content, calcium hypochlorite is particularly preferred. The higher strength granular forms of the product (containing 65-75% available chlorine) are most preferred.

Under such strongly acidic conditions (pH between about −1 and about 5), the oxidation reaction written at reaction (21) is virtually instantaneous and proceeds to completion in a short time.

$$NH_2-SO_3H + 2HBr + Ca(OCl)_2 \rightarrow [Br][NH-SO_3H] + CaCl_2 + H_2O \qquad (21)$$

The calcium hypochlorite is preferably added to the reactor rapidly and with good mixing in order to minimize loss of bromine vapors from the reaction medium but not too quickly such that phase separation of elemental bromine becomes apparent at the bottom of the reactor. The granular form of solid calcium hypochlorite facilitates the transfer of the product into the reaction vessel. As it reacts, the coarse granules disappear, and the reaction is considered to be complete when no more coarse granules are evident. When this occurs, all the sulfamic acid has reacted to yield a bromo-sulfamic acid complex.

f. Removing any insoluble reaction by-products with a conventional solid-liquid separation technique.

Any suitable solid-liquid separation technique can be employed. Suitable examples include, but are not limited to, centrifugation, clarification, gravity sedimentation, and vacuum filtration. Filtration is a particularly preferred technique for effecting solid-liquid separation. When the solid inorganic halogenating agent is calcium hypochlorite, insoluble reaction by-products include calcium carbonate, lime, and quicklime. Filtration of the reaction medium is carried out at pH 1-9, but preferably at about pH 4-8 to mitigate the problem of $CO_2$ gas being liberated from calcium carbonate and also minimize the amount of bromine vapor that is emitted from the reaction medium.

g. Adding an alkaline source to the reaction mother liquors such that if the alkaline source is a hydroxide salt, the overall mole ratio of aqueous hydrogen bromide to hydroxide is between about 1:2 and about 1:4, preferably between about 1:3 and about 1:4.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F. The purpose is to deprotonate the bromo derivative of sulfamic acid to form the bromo derivative of sodium sulfamate according to reaction (22).

$$[Br][NH-SO_3H] + NaOH \rightarrow [Br][NH-SO_3^-][Na^+] + H_2O \qquad (22)$$

The amount of 50% NaOH solution employed depends on the initial charge of aqueous hydrogen bromide. The overall mole ratio of aqueous hydrogen bromide to NaOH added in steps (d) and (g) is in the range of about 1:2 to about 1:4, preferably about 1:3 to about 1:4.

Examples 10-11

A general procedure for preparing the liquid stabilized bromine concentrates listed in Table III is as follows:

To a stirred reaction flask containing 48% HBr, the appropriate amount of 50% hydrogen peroxide was added dropwise at a rate such that the temperature did not exceed 142° F. After allowing the reaction flask to cool to around 95° F., solid sulfamic acid was introduced. The resulting slurry was stirred as the appropriate amount of 50% NaOH solution was charged to the reaction flask that was cooled so the temperature did not exceed 85° F. Thereafter, the correct amount of granular calcium hypochlorite (59.5% available chlorine) was introduced, also with stirring. Upon filtration of insolubles, sufficient 50% NaOH and solid NaOH was slowly introduced so that the overall mole ratio of aqueous hydrogen bromide to hydroxide was 1:3. During the addition, the reaction flask was cooled on ice so that the temperature of the contents did not exceed 80-90° F. Iodometric titration of the resultant golden yellow solutions was used to determine the weight % $Br_2$ (or $Cl_2$) contents. The theoretical amounts of $Br_2$ (or $Cl_2$ equivalent) produced as a function of the sum of the hydrogen peroxide and calcium hypochlorite charges were then used to compute the % yield of each reaction.

TABLE III

| Example | Mass 50% $H_2O_2$/g | Mass 48% HBr/g | Mass sulfamic acid/g | Mass $Ca(OCl)_2$ (59.5% av. $Cl_2$)/g | Mass NaOH/g (1) $1^{st}$ (2) $2^{nd}$ | Wt. % as $Br_2$ ($Cl_2$) | % Yield |
|---|---|---|---|---|---|---|---|
| 10 | 4.22 | 27.82 | 19.2 | 11.0 | (1) 13 g 50% (2) 10 g 50% + 10 g 100% | 21.6 (9.6) | 83.5 |
| 11 | 8.48 | 55.6 | 38.4 | 24.22 | (1) 26 g 50% (2) 8 g 50% + 13 g 100% | 21.3 (9.48) | 70.8 |

4. The Method of Preparing a Mixed Halogen Composition Using a Solid Organic Chlorinating Agent The method preferably includes the following steps. Steps (a), (b), and (c) may be performed in any order, or simultaneously, followed by the remaining steps.

a. Utilizing an aqueous solution of bromide ions in which the pH is less than +1.

The first step of this method is conducted under conditions of extreme acidity, preferably at a pH which is greater than −1 and less than +1. Any acidified source of bromide ions can be employed in the practice of this invention, for example, an aqueous solution of sodium bromide acidified with a strong mineral acid such as hydrochloric or nitric acid. However, aqueous hydrogen bromide is a preferred starting material and can be used at any concentration up to 70% by weight, although 48% is especially convenient to use as this is the concentration at which the product does not appreciably fume HBr vapors.

b. Introducing to the highly acidic solution of bromide ions, a highly concentrated solution of hydrogen peroxide to effect a partial or complete oxidation of the bromide ions into bromine.

$$2HBr(aq) + H_2O_2 \rightarrow Br_2 + 2H_2O \tag{23}$$

Strong solutions of hydrogen peroxide are preferably introduced to the 48% aqueous hydrogen bromide solution, although the order of addition can be changed without appreciably effecting the reaction. Hydrogen peroxide is commercially available at concentrations up to 90%, but 50% hydrogen peroxide is safer to use and is more commonly available. Preferably, 50% hydrogen peroxide is added slowly and with stirring to a solution of 48% aqueous hydrogen bromide calculated to have a pH of −0.78. The amount of 50% hydrogen peroxide added to the 48% aqueous hydrogen bromide solution should be sufficient to oxidize between 10% and 100% of the stoichiometric amount and, most preferably, between 20% and 80% of the stoichiometric amount of bromide ions into bromine. The oxidation of aqueous hydrogen bromide with hydrogen peroxide is an exothermic reaction. Heat removal is effected by conducting the reaction at the refluxing temperature of the reaction medium using a condenser to facilitate the heat removal process. Alternatively, cooling is effected with a jacketed reactor. The reaction time and temperature are controlled in order to maximize the conversion of bromide into bromine and minimize the amount of unreacted hydrogen peroxide remaining in the reaction medium.

When hydrogen peroxide is used in this fashion, all of the Br moieties introduced to the reactor as hydrobromic acid materialize as active bromine in the final product. None are wasted as by-product bromide ion salts.

c. Mixing a complexing agent to the fully or partially oxidized solution.

On allowing the highly acidic, bromine-laden reaction mixture to cool, a complexing agent is introduced to the same reactor. Preferably the complexing agent is solid sulfuric acid. Bromine reacts with sulfamic acid to form a bromo-derivative and co-produces an additional amount of hydrogen bromide as illustrated by reaction (24).

$$Br_2 + NH_2-SO_3H \rightarrow [Br][NH-SO_3H] + HBr \tag{24}$$

The amount of sulfamic acid added depends on the amount total halogen required in the final product. A mole ratio of about 0.75:1 to about 1.5:1 sulfamic acid to total halogen is advantageous to the stability of the final product, with about 0.95:1 to about 1.2:1 being the most preferred mole ratio range.

d. Adding an alkaline source to the reaction medium to adjust its pH to between about 0.5 and about 9 and preferably between about 1.0 and about 4.5.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F. The purpose is to deprotonate the bromo derivative of sulfamic acid to form the bromo derivative of sodium sulfamate according to reaction (25).

$$[Br][NH-SO_3H] + NaOH \rightarrow [Br][NH-SO_3^-][Na^+] + H_2O \tag{25}$$

e. Introducing sufficient solid, organic chlorinating agent to complete the oxidation of the bromide ions into bromine (if the solution is only partially oxidized in step (b)), and to release soluble chlorine into the solution by complexing with sulfamic acid.

The molar equivalent of the combination of hydrogen peroxide added in step (b) and solid chlorinating agent should be in excess of the molar equivalent of bromide ions added in step (a). Employing a 10% molar excess of the combination of hydrogen peroxide and solid organic chlorinating agent over the bromide ions, yields a mixed halogen composition of 90 mole % bromine and 10 mole % chlorine.

Solid organic chlorinating agents include any organic compound in which the chlorine atom is in oxidation state +1 and is covalently bound to a nitrogen or phosphorus atom within the same molecule. Suitable examples include, but are not limited to, trichloroisocyanuric acid (TCCA), sodium dichloroisocyanurate (NaDCC), sodium dichloroisocyanurate dihydrate (NaDCC.2H$_2$O), potassium dichloroisocyanurate (KDCC), dichloroisocyanuric acid (DCCA), trichloromelamine, N-chloro-p-toluenesulfonamide, N-chloromethanesulfonamide, N-chlorosuccinimide, N,N'-1,3-bromochloro-5,5-dimethylhydantoin, N,N'-1,3-bromochloro-5-ethyl-5-methylhydantoin, and 1,3-dichloro-5,5-dimethylhydantoin. A particularly preferred source of a solid, organic chlorinating agent is trichloroisocyanuric acid (TCCA). In completing the oxidation of hydrogen bromide solution, TCCA reacts according to the following equation.

$$\text{NH}_2\text{—SO}_3\text{H} + \text{HBr} + \text{TCCA} \rightarrow [\text{Br}][\text{NH—SO}_3\text{H}] + \text{Cl}^- + \text{Cyanuric Acid} \quad (26)$$

In releasing soluble chlorine into the aqueous solution by complexing with sulfamic acid, it reacts according to equation (27).

$$\text{NH}_2\text{—SO}_3\text{—H} + \text{TCCA} \rightarrow [\text{Cl}][\text{NH—SO}_3\text{H}] + \text{H}_2\text{O} + \text{Cyanuric Acid} \quad (27)$$

Preferably TCCA is used in the form of a coarse granular grade of material for ease of introduction to the stirred, cooled reactor. As the TCCA reacts, the coarse granules disappear. The reaction is considered to be complete when no more coarse granules are evident. Although granular TCCA is favored because of its easy handling characteristics, and for providing a visual signal that the reaction is complete, TCCA powdered wetcake may also be employed. The advantage of using TCCA powdered wetcake is that it may be taken directly from the TCCA-producing reactors to eliminate costs associated with drying and granulation of the material.

f. Removing any insoluble reaction by-products with a conventional solid-liquid separation technique.

Any suitable solid-liquid separation technique can be employed. Suitable examples include, but are not limited to, centrifugation, clarification, gravity sedimentation, and vacuum filtration. Filtration is a particularly preferred technique for effecting solid-liquid separation. When the solid organic chlorinating agent is TCCA, cyanuric acid (CA) is a reaction by-product that is insoluble in the reaction medium (see reactions (26) and (27)). Filtration of the cyanuric acid residue is carried out at pH 1-9, but preferably at pH 1.5-4.5 to maximize CA recovery from solution and minimize the amount of bromine vapor that fumes from the reaction medium. Upon washing the filtercake with water to remove the mother liquors, a highly pure CA wetcake is recovered. This can be recycled to other processes in order to make additional quantities of TCCA, NaDCC, or NaDCC.2H$_2$O that can be used in the method of the current invention.

If desired, this step can be modified so that the sodium salt of cyanuric acid is recovered from the reaction medium instead of cyanuric acid. This is accomplished by introducing, before performing the solid-liquid separation, sufficient 50% NaOH to react with cyanuric acid according to the following equation:

$$\text{CA} + \text{NaOH} \rightarrow \text{NaCA} + \text{H}_2\text{O} \quad (28)$$

The amount of 50% sodium hydroxide solution employed depends on the amount of solid organic chlorinating agent used in step (e) that is introduced to oxidize all or substantially all of the remaining bromide ions into bromine, and to release soluble chlorine into the aqueous solution by complexing with sulfamic acid, When TCCA is the solid organic chlorinating agent, sufficient 50% NaOH solution is introduced slowly with mixing and cooling to convert all or substantially all of the cyanuric acid liberated in reactions (26) and (27) into its monosodium salt via reaction (28). Monosodium cyanurate is insoluble in the reaction medium at pH<9. As is true of cyanuric acid, monosodium cyanurate can be separated and recycled to other processes in order to make additional quantities of TCCA, NaDCC, or NaDCC.2H$_2$O that can be used in the method of the current invention. This is accomplished by performing a solid-liquid separation, as described above, which is done when the pH stabilizes at about 9.

g. Adding an alkaline source to the reaction mother liquors such that if the alkaline source is a hydroxide salt, the mole ratio of chlorine that is equivalent to the combination of hydrogen peroxide and solid organic chlorinating agent to the hydroxide added in steps (d) and (g) is between about 1:2 and about 1:5, preferably between about 1:3 and about 1:4. This does not include any hydroxide salt that may be used to convert cyanuric acid into its alkali metal or earth alkali metal salt as described in step (f).

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F. The purpose is to deprotonate the halo derivatives of sulfamic acid to form the halo derivatives of sodium sulfamate according to reaction (29).

$$[\text{X}][\text{NH—SO}_3\text{H}] + \text{NaOH} \rightarrow [\text{X}][\text{NH—SO}_3^-][\text{Na}^+] + \text{H}_2\text{O} \quad (29)$$

X=Br and Cl

The amount of 50% NaOH solution depends on the amount of hydrogen peroxide and solid organic chlorinating agent employed. The overall mole ratio of chlorine that is equivalent to the combination of hydrogen peroxide and solid organic chlorinating agent to the hydroxide added in steps (d) and (g) is between about 1:2 and about 1:5, preferably between about 1:3 and about 1:4. This does not include any 50% NaOH solution that may be used to convert cyanuric acid into its monosodium salt as described in step (f).

h. Removing any further insoluble residues that develop with a conventional solid-liquid separation technique.

As noted above, any suitable solid-liquid separation technique may be employed. Generally, when TCCA is the chlorinating agent, almost 90% of CA reaction by-product is recovered as a highly pure wetcake in the first solid-liquid separation described in step (f). While not wishing to be bound by theory, it is believed that salts of cyanuric acid are precipitated from the reaction mother liquors upon the addition of alkaline sources. When the alkaline source is, for example, 50% sodium hydroxide solution, the mono-, di-, and trisodium salts of cyanuric acid are precipitated. Although insoluble in the reaction mother liquors, the di and trisodium salts display exceptional solubility in ordinary water and are thus useful water treating agents in their own right. However, in comparison to the amount of solids recovered in step (f), the amount of solid that may subsequently develop is relatively low and step (h) may require only a polishing solid-liquid separation, with, for example, a cartridge filter. Moreover, the two solid-liquid separation steps of (f) and (h) may be combined into a single operation performed only at step (f).

5. The Method of Preparing a Mixed Halogen Composition Using a Solid Inorganic Chlorinating Agent The method preferably includes the following steps. Steps (a), (b), and (c) may be performed in any order, or simultaneously, followed by the remaining steps.

a. Utilizing an aqueous solution of bromide ions in which the pH is less than +1.

The first step of this method is conducted under conditions of extreme acidity, preferably at a pH which is greater than −1 and less than +1. Any acidified source of bromide ions can be employed in the practice of this invention, for example, an aqueous solution of sodium bromide acidified with a strong mineral acid such as hydrochloric or nitric acid. However, aqueous hydrogen bromide is a preferred starting material and can be used at any concentration up to 70% by weight, although 48% is especially convenient to use as this is the concentration at which the product does not appreciably fume HBr vapors.

b. Introducing to the highly acidic solution of bromide ions, a highly concentrated solution of hydrogen peroxide to effect a partial or complete oxidation of the bromide ions into bromine.

$$2HBr(aq) + H_2O_2 \rightarrow Br_2 + 2H_2O \tag{30}$$

Strong solutions of hydrogen peroxide are preferably introduced to the 48% aqueous hydrogen bromide solution, although the order of addition can be changed without appreciably effecting the reaction. Hydrogen peroxide is commercially available at concentrations up to 90%, but 50% hydrogen peroxide is safer to use and is more commonly available. Preferably, 50% hydrogen peroxide is added slowly and with stirring to a solution of 48% aqueous hydrogen bromide calculated to have a pH of −0.78. The amount of 50% hydrogen peroxide added to the 48% aqueous hydrogen bromide solution should be sufficient to oxidize between 10% and 100% of the stoichiometric amount and, most preferably, between 20% and 80% of the stoichiometric amount of bromide ions into bromine. The oxidation of aqueous hydrogen bromide with hydrogen peroxide is an exothermic reaction. Heat removal is effected by conducting the reaction at the refluxing temperature of the reaction medium using a condenser to facilitate the heat removal process. Alternatively, cooling is effected with a jacketed reactor. The reaction time and temperature are controlled in order to maximize the conversion of bromide into bromine and minimize the amount of unreacted hydrogen peroxide remaining in the reaction medium.

When hydrogen peroxide is used in this fashion, all of the Br moieties introduced to the reactor as hydrobromic acid can materialize as active bromine in the final product. None are wasted as by-product bromide ion salts.

c. Mixing a complexing agent to the fully or partially oxidized solution.

On allowing the highly acidic, bromine-laden reaction mixture to cool, a complexing agent is introduced to the same reactor. Preferably the complexing agent is solid sulfamic acid. Bromine reacts with sulfamic acid to form a bromo derivative and co-produces an additional amount of hydrogen bromide as illustrated by reaction (31).

$$Br_2 + NH_2-SO_3H \rightarrow [Br][NH-SO_3H] + HBr \tag{31}$$

The amount of sulfamic acid added depends on the amount total halogen required in the final product. A mole ratio of about 0.75:1 to about 1.5:1 sulfamic acid to total halogen is advantageous to the stability of the final product, with about 0.95:1 to about 1.2:1 being the most preferred mole ratio range.

d. Adding an alkaline source to the reaction mother liquors such that if the alkaline source is a hydroxide salt, the overall mole ratio of aqueous hydrogen bromide to hydroxide is between about 0.5:1 and about 1:2, preferably about 1:1.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F. The purpose is to deprotonate the bromo derivative of sulfamic acid to form the bromo derivative of sodium sulfamate according to reaction (32).

$$[Br][NH-SO_3H] + NaOH \rightarrow [Br][NH-SO_3^-][Na^+] + H_2O \tag{32}$$

e. Introducing sufficient solid, inorganic chlorinating agent to complete the oxidation of the bromide ions into bromine (if the solution is only partially oxidized in step (b)), and to release soluble chlorine into the solution by complexing with sulfamic acid.

The molar equivalent of the combination of hydrogen peroxide added in step (b) and solid chlorinating agent should be in excess of the molar equivalent of bromide ions added in step (a). Employing a 10% molar excess of the combination of hydrogen peroxide and solid inorganic chlorinating agent over the bromide ions, yields a mixed halogen composition of 90 mole % bromine and 10 mole % chlorine.

Solid inorganic chlorinating agents include, but are not limited to, alkali metal and earth alkali metal hypochlorite salts. Suitable examples include lithium hypochlorite, calcium hypochlorite, and magnesium hypochlorite. Due to its low cost and high available chlorine content, calcium hypochlorite is particularly preferred. The higher strength granular forms of the product (containing 65-75% available chlorine) are most preferred.

In completing the oxidation of hydrogen bromide solution, $Ca(OCl)_2$ reacts according to the following equation.

$$NH_2SO_3H + 2HBr + Ca(OCl)_2 \rightarrow [Br][NH-SO_3H] + CaCl_2 + H_2O \tag{33}$$

Under such strongly acidic conditions (pH between about −1 and about 5), the oxidation reaction written at reaction (33) is virtually instantaneous and proceeds to completion in a short time.

In releasing soluble chlorine into the aqueous solution by complexing with sulfamic acid, calcium hypochlorite reacts according to equation (34).

$$NH_2-SO_3-H + Ca(OCl)_2 \rightarrow [Cl][HN-SO_3H] + H_2O \tag{34}$$

The calcium hypochlorite is preferably added to the reactor rapidly and with good mixing in order to minimize loss of bromine vapors from the reaction medium but not too quickly such that phase separation of elemental bromine becomes apparent at the bottom of the reactor. The granular form of solid calcium hypochlorite facilitates the transfer of the product into the reaction vessel. As it reacts, the coarse granules disappear, and the reaction is considered to be complete when no more coarse granules are evident. When this occurs, all the sulfamic acid has reacted to yield mixed halogen-sulfamic acid complexes.

f. Removing any insoluble reaction by-products with a conventional solid-liquid separation technique.

Any suitable solid-liquid separation technique can be employed. Suitable examples include, but are not limited to, centrifugation, clarification, gravity sedimentation, and vacuum filtration. Filtration is a particularly preferred technique for effecting solid-liquid separation. When the solid inorganic chlorinating agent is calcium hypochlorite, insoluble reaction by-products include calcium carbonate, lime, and quicklime. Filtration of the reaction medium is carried out at pH 1-9, but preferably at about pH 4-8 to mitigate the problem of $CO_2$ gas being liberated from calcium carbonate and also minimize the amount of bromine vapor that is emitted from the reaction medium.

g. Adding an alkaline source to the reaction mother liquors such that if the alkaline source is a hydroxide salt, the mole ratio of chlorine that is equivalent to the combination of hydrogen peroxide and solid inorganic chlorinating agent to the hydroxide added in steps (d) and (g) is between about 1:2 and about 1:5, preferably between about 1:3 and about 1:4.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F. The purpose is to deprotonate the halo derivatives of sulfamic acid to form the halo derivatives of sodium sulfamate according to reaction (35).

$$[X][NH-SO_3H] + NaOH \rightarrow [X][NH-SO_3^-][Na^+] + H_2O \quad (35)$$

X=Br and Cl

The Third Embodiment

This embodiment is a method of preparing a concentrated liquid bromine-containing biocide composition using a solution of bromide ions and a solid halogenating agent (either organic or inorganic). This golden-colored composition contains 60-80% more available bromine than solutions that are currently available commercially. Moreover, the aqueous composition contains the highest concentration of bromine hitherto reported in the prior art. Typically, the composition of this invention contains greater than 18% as $Br_2$ (8% as $Cl_2$).

This method of this embodiment may also be used to prepare a liquid mixed halogen composition that contains both bromine and chlorine. The method uses a source of bromide ions in conjunction with a molar excess of a solid chlorinating agent (either organic or inorganic). This light golden-colored composition contains 60-80% more available halogen than the all-bromine solutions that are currently available commercially. Typically, the mixed halogen composition prepared using this method contains a total halogen level of greater than 9.4% expressed as $Cl_2$ (21% expressed as $Br_2$)

A major benefit of a mixed halogen biocide is in the treatment of contaminated water that exerts a considerable halogen demand. This chemical demand can be satisfied by the less expensive chlorine portion of the composition, permitting more of the bromine portion to be available for microbiological control. Mixed halogen compositions are also safer and more convenient to manufacture than those that are predominantly bromine based. For example, during the preparation of the latter, the solutions have a tendency to emit deep red, highly corrosive and toxic bromine fumes right up until the final addition of the alkaline source. These vapors must be scrubbed from the reaction vessel's headspace in order to eliminate atmospheric release, worker exposure, and to prevent the fumes from entering and damaging expensive vacuum processing equipment. By contrast, the mixed halogen compositions emit hardly any deep red bromine fumes during their manufacture. Thus, the necessity for scrubbing the reaction vessel's headspace is eliminated.

A further significant aspect of compositions based on mixtures of stabilized bromine and chlorine is that in water systems employing long contact times, there may be sufficient time for the N-chlorosulfamate to react with "spent" bromide ion and regenerate N-bromosulfamate according to the following schematic.

Upon performing biocidal and oxidative reactions, HOBr reverts to soluble bromide ion. This can enter into reaction with N-chlorosulfamate to generate additional N-bromosulfamate

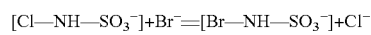

In this way the consumer is able to derive the performance benefits of 2 moles of N-bromosulfamate for the price of 1 mole of N-bromosulfamate and 1 mole of N-chlorosulfamate.

As a general rule, chlorinated compounds display higher water solubility than their brominated counterparts. Further, a mixed halogen composition may be formulated to employ far less sodium bromide salt than an all-bromine solution. Thus, another highly advantageous facet of this invention is that it makes possible the formation of a mixed halogen composition that is lower in solids and is inherently more soluble than those based solely on bromine. This highly water-soluble composition exhibits improved physical stability as it becomes less prone to solid precipitation on storage.

The method preferably includes the following steps. Steps (a), (b), and (c) or steps (a), (b), and (d) may be performed in any order, or simultaneously, followed by the remaining steps.

a. Utilizing an alkali metal or earth alkali metal solution of bromide ions.

Sources of alkali metal or earth alkali metal solutions of bromide ions include, but are not limited to, lithium bromide, sodium bromide, potassium bromide, calcium bromide, and magnesium bromide. A preferred source of bromide ion solution is sodium bromide solution, commonly available as a 40-46% aqueous solution, or it may be made into such a solution by dissolving solid sodium bromide salt in water.

b. Mixing a complexing agent to the bromide ion solution.

Preferably the complexing agent is sulfamic acid. The amount of sulfamic acid added depends on the amount of bromide ion originally present. A mole ratio of about 0.75:1 to about 1.5:1 sulfamic acid to sodium is advantageous to the stability of the final product with about 0.95:1 to about 1.2:1 being the most preferred mole ratio range.

The next step is either (c) or (d).

c. Adding an alkaline source to the reaction medium to adjust its pH to between about 0.5 and about 9 and preferably between about 1.0 and about 4.5, followed by introducing sufficient solid, organic halogenating agent to oxidize all or substantially all of the bromide ions into bromine.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F.

Solid organic halogenating agents include any organic compound in which one or more halogen atoms such as Cl, Br, or I is present in oxidation state +1 and is covalently bound to a nitrogen or phosphorus atom within the same molecule. Suitable examples include, but are not limited to, trichloroisocyanuric acid (TCCA), sodium dichlorisocyanurate (NaDCC), sodium dichlorisocyanurate dihydrate (NaDCC.2H$_2$O), trichloromelamine, N-chloro-p-toluenesulfonamide, N-chloromethanesulfonamide, N-chlorosuccinimide, N,N'-1,3-bromochloro-5,5-dimethylhydantoin, N,N'-1,3-bromochloro-5-ethyl-5-methylhydantoin, 1,3-dibromo-5,5-dimethylhydantoin, 1,3-dichloro-5,5-dimethylhydantoin, and N-bromosuccinimide. A particularly preferred source of a solid, organic halogenating agent is trichloroisocyanuric acid (TCCA). Preferably this is used in the form of a coarse granular grade of material for ease of introduction to the stirred, cooled reactor. As the TCCA reacts, the coarse granules disappear. The reaction is considered to be complete when no more coarse granules are evident. Although dry, granular TCCA is favored because of its easy handling characteristics, and for providing a visual signal that the reaction is complete, TCCA powdered wetcake may also be employed. The advantage of using TCCA wetcake is that it may be taken directly from the TCCA-producing reactors and so costs associated with drying and granulation of the material are eliminated.

$$\text{NaBr} + \text{NaOH} + \text{NH}_2\text{—SO}_3\text{H} + \text{TCCA} \rightarrow [\text{Br}][\text{NH—SO}_3\text{H}] + \text{NaCl} + \text{H}_2\text{O} + \text{Cyanuric Acid} \quad (36)$$

In order to prepare a mixed halogen solution, a molar excess of organic chlorinating agent to bromide ions is employed. Employing a 10% molar excess of the solid organic chlorinating agent over the bromide ions, yields a mixed halogen composition of 90 mole % bromine and 10 mole % chlorine. Suitable examples include, but are not limited to, trichloroisocyanuric acid (TCCA), sodium dichlorisocyanurate (NaDCC), sodium dichlorisocyanurate dihydrate (NaDCC.2H$_2$O), trichloromelamine, N-chloro-p-toluenesulfonamide, N-chloromethanesulfonamide, N-chlorosuccinimide, N,N'-1,3-bromochloro-5,5-dimethylhydantoin, N,N'-1,3-bromochloro-5-ethyl-5-methylhydantoin, and 1,3-dichloro-5,5-dimethylhydantoin. In this case, the organic chlorinating agent has dual functionality. First, it oxidizes all of the bromide ions into bromine which reacts with the sulfamic acid to form N-bromosulfamic acid as indicated in reaction (36). Second, the excess chlorinating agent releases soluble chlorine into the aqueous solution by complexing with sulfamic acid to form N-chlorosulfamic acid according to reaction (37).

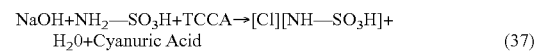

$$\text{NaOH} + \text{NH}_2\text{—SO}_3\text{H} + \text{TCCA} \rightarrow [\text{Cl}][\text{NH—SO}_3\text{H}] + \text{H}_2\text{O} + \text{Cyanuric Acid} \quad (37)$$

If step (c) is used, step (d) is not used. If step (c) is not used, step (d) is used.

d. Introducing sufficient solid inorganic halogenating agent to oxidize all or substantially all of the bromide ions into bromine.

Solid inorganic halogenating agents include, but are not limited to, alkali metal and earth alkali metal hypochlorite salts. Suitable examples include lithium hypochlorite, calcium hypochlorite, and magnesium hypochlorite. Due to its low cost and high available chlorine content, calcium hypochlorite is particularly preferred. The higher strength granular forms of the product (containing 65-75% available chlorine) are most preferred.

Under acidic conditions (pH between about −1 and about 5), the oxidation reaction is virtually instantaneous, and proceeds to completion in a short time. The calcium hypochlorite is preferably added rapidly and with good mixing in order to minimize loss of bromine vapors from the reaction mixture but not too quickly such that that phase separation of elemental bromine becomes apparent at the bottom of the reactor. When the addition of the calcium hypochlorite is complete, all the sulfamic acid has solubilized to yield an acidic reaction mixture. Preferably it is used in the form of a coarse granular grade for ease of introduction to the stirred, cooled reactor. As the calcium hypochlorite reacts, the coarse granules disappear. The reaction is considered to be complete when no more coarse granules are evident.

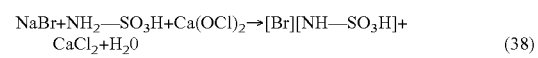

$$\text{NaBr} + \text{NH}_2\text{—SO}_3\text{H} + \text{Ca(OCl)}_2 \rightarrow [\text{Br}][\text{NH—SO}_3\text{H}] + \text{CaCl}_2 + \text{H}_2\text{O} \quad (38)$$

In order to prepare a mixed halogen solution, a molar excess of inorganic chlorinating agent to bromide ions is employed. Employing a 10% molar excess of the solid inorganic chlorinating agent over the bromide ions, yields a mixed halogen composition of 90 mole % bromine and 10 mole % chlorine. Suitable examples include lithium hypochlorite, calcium hypochlorite, and magnesium hypochlorite. In this case, the inorganic chlorinating agent has dual functionality. First, it oxidizes all of the bromide ions into bromine which reacts with the sulfamic acid to form N-bromosulfamic acid as indicated in reaction (38). Second, the excess chlorinating agent releases soluble chlorine into the aqueous solution by complexing with sulfamic acid to form N-chlorosulfamic acid according to reaction (39).

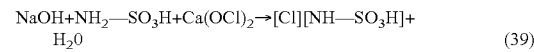

$$\text{NaOH} + \text{NH}_2\text{—SO}_3\text{H} + \text{Ca(OCl)}_2 \rightarrow [\text{Cl}][\text{NH—SO}_3\text{H}] + \text{H}_2\text{O} \quad (39)$$

e. Removing any insoluble reaction by-products with a conventional solid-liquid separation technique.

Any suitable solid-liquid separation technique can be employed. Suitable examples include, but are not limited to, centrifugation, clarification, gravity sedimentation, and vacuum filtration. Filtration is a particularly preferred technique for effecting solid-liquid separation.

When the solid organic halogenating agent is TCCA, cyanuric acid is a reaction by-product that is insoluble in the reaction medium (see reactions (36) and (37)). Filtration of the cyanuric acid (CA) residue is carried out at pH 1-9, but preferably at pH 1-6 to maximize its recovery from solution and minimize the amount of bromine vapors that fume from the reaction medium. Upon washing the filtercake with water to remove the mother liquors, a highly pure CA wetcake is recovered. This can be recycled to other processes to make additional quantities of TCCA, NaDCC, or NaDCC.2H$_2$O that can be used in the method of the current invention.

If desired, this step can be modified so that the sodium salt of cyanuric acid is recovered from the reaction medium instead of cyanuric acid. This is accomplished by introducing, before performing the solid-liquid separation, sufficient 50% NaOH to react with cyanuric acid according to the following equation:

$$CA + NaOH \rightarrow NaCA + H_2O \quad (40)$$

The amount of 50% sodium hydroxide solution employed depends on the amount of solid organic halogenating or chlorinating agent used in step (c). When TCCA is the solid organic halogenating or chlorinating agent, sufficient 50% NaOH solution is introduced slowly with mixing and cooling to convert all or substantially all of the cyanuric acid liberated in equations (36) and (37) into its monosodium salt via reaction (40). Monosodium cyanurate is insoluble in the reaction medium at pH<9. As is true of cyanuric acid, monosodium cyanurate can be separated and recycled to other processes in order to make additional quantities of TCCA, NaDCC, or NaDCC.2H$_2$O that can be used in the method of the current invention. This is accomplished by performing a solid-liquid separation, as described above, which is done when the pH stabilizes at about 9.

When the solid inorganic halogenating agent is calcium hypochlorite, insoluble reaction by-products include calcium carbonate, lime, and quicklime. Filtration of the reaction medium is carried out at pH 1-9, but preferably at pH 4-8 to mitigate the problem of CO$_2$ gas being liberated from calcium carbonate and also minimize the amount of bromine vapors that fume from the reaction medium.

f. Adding an alkaline source to the reaction mother liquors.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used. The sodium hydroxide solution is introduced to the reaction medium slowly, and with stirring and cooling such that the temperature preferably does not exceed 80° F.

To prepare the all-bromine-containing liquid composition, and if the alkaline source is a hydroxide salt, the overall mole ratio of bromide ion to hydroxide added in steps (c) (if used) and (f) is between about 1:2 and about 1:4, preferably between about 1:3 and about 1:4. This does not include any hydroxide salt that may be used to convert cyanuric acid into its alkali metal or earth alkali metal salt as described in step (e).

To prepare the liquid mixed halogen composition, and if the alkaline source is a hydroxide salt, the overall mole ratio of chlorine equivalent to hydroxide added in steps (c) (if used) and (f) is between about 1:2 and about 1:4, preferably between about 1:3 and about 1:4. This does not include any hydroxide salt that may be used to convert cyanuric acid into its alkali metal or earth alkali metal salt as described in step (e).

In either case, the purpose is to deprotonate the halo derivatives of sulfamic acid to form the halo derivatives of sodium sulfamate according to reaction (41).

$$[X][NH-SO_3H] + NaOH \rightarrow [X][NH-SO_3^-][Na^+] + H_2O \quad (41)$$

X=Br and Cl g. Removing any further insoluble residues that develop with a conventional solid-liquid separation technique.

As noted above, any suitable solid-liquid separation technique may be employed. Generally, when TCCA is the halogenating agent, almost 90% of CA reaction by-product is recovered as a highly pure wetcake in the first solid-liquid separation operation described in step (e). While not wishing to be bound by theory, it is believed that salts of cyanuric acid are precipitated from the reaction mother liquors upon the addition of alkaline sources. When the alkaline source is, for example, 50% sodium hydroxide solution, the mono-, di-, and trisodium salts of cyanuric acid are precipitated. Although insoluble in the reaction mother liquors, the di and trisodium salts display exceptional solubility in ordinary water and are thus useful water treating agents in their own right. However, in comparison to the amount of solids recovered in step (e), the amount of solid that may subsequently develop is relatively low and step (g) may require only a polishing solid-liquid separation, with, for example, a cartridge filter. Moreover, the two solid-liquid separation steps of (e) and (g) may be combined into a single operation performed only at step (e).

Examples 12-13

A general procedure for preparing the liquid stabilized bromine concentrates listed in Table IV is as follows:

To a stirred reaction flask containing 40% NaBr (25.7 g) was added deionized water (30 g) and solid sulfamic acid (11.7 g). The resulting slurry was stirred as 50% sodium hydroxide solution (9.65 g) was charged to the reaction flask to give a pH of 2.0. The flask was chilled during this process so that the temperature did not exceed 80-90° F. A single charge of granular trichlorocyanuric acid (7.74 g) was then introduced to the reaction flask.

In an alternate process, the step of introducing 50% sodium hydroxide was omitted, and calcium hypochlorite (10.67 g) was added to the reaction flask in place of TCCA. Within 15-30 minutes, fine powdery precipitates had developed in both cases. The solids were removed by vacuum filtration and the filter cakes were washed with copious amounts of deionized water to remove reaction mother liquors and dissolved salts. Then the appropriate amount of 50% NaOH solution was introduced to the filtered solution with cooling, and at a rate such that the temperature did not exceed 80-90° F. Any additional residues that developed were also removed by vacuum filtration. Iodometric titration of the resultant golden yellow solutions was used to determine their bromine content. The respective yields were calculated using the weight and assay of TCCA or Ca(OCl)$_2$ used in the initial charge to the reaction flask. Table IV summarizes the data obtained.

TABLE IV

| Example | Reactant | Reactant assay/% as av.Cl$_2$ | Initial 50% NaOH charge/g | Final 50% NaOH charge/g | Wt. % Br$_2$ (Cl$_2$) | % Yield |
|---|---|---|---|---|---|---|
| 12 | TCCA | 90 | 9.65 | 10.0 | 14.76 (6.56) | 85.0* |
| 13 | Ca(OCl)$_2$ | 59.5 | 0 | 22.0 | 14.4 (6.4) | 100.9 |

*From the weight of the dry filter cake, it was calculated that 88.5% of the cyanuric acid (CA) charged to the reaction flask as TCCA was recovered in the first filtration.

Example 14

This example represents a scale-up of the reaction described in example 12.

To a stirred reaction flask containing 40% NaBr solution (182 g) was added deionized water (40 g) and solid sulfamic acid (82.4 g). The reaction medium was stirred and cooled as 50% sodium hydroxide solution (60.2 g) was slowly introduced such that the temperature did not exceed 85° F. A single charge of granular trichloroisocyanuric acid (55 g) was then added to the reaction flask that was stirred for around 20 minutes. All of the coarse TCCA granules were observed to have reacted within this period as a fine powdery precipitate developed. Prior to filtration, the pH of the reaction liquors was adjusted to 1.55 by addition of more 50% NaOH solution (5.0 g). Upon filtration of the insolubles, the filtercake was washed with two bed volumes of deionized water. The wash liquors were discarded, and the filter wetcake was placed in an oven to dry overnight at 130° F. To the filtrates was added additional 50% NaOH (90 g) again with cooling and stirring and at a rate such that the temperature of the reaction did not exceed 80-90° F. Any additional solids that precipitated from solution were removed by vacuum filtration, immediately upon completing the addition of the 50% NaOH. Iodometric titration of the resultant golden solution yielded a $Br_2$ content of 22.7% (or 10.1% as $Cl_2$). The theoretical amount of $Br_2$ (or $Cl_2$ equivalent) produced as a function of the amount of TCCA charged was used to compute a reaction yield of 98.8%. The weight of the dry solids removed on the first filtration indicated that 86.6% of the cyanuric acid had been recovered.

Example 15

This example describes the preparation of a mixed halogen composition that contains both bromine and chlorine. The same conditions as those listed in Example 14 are employed except for using half the amount of NaBr.

To a stirred reaction flask containing 40% NaBr solution (91 g) was added deionized water (131 g) and solid sulfamic acid (82.4 g). The reaction medium was stirred and cooled as 50% sodium hydroxide solution (60.2 g) was slowly introduced such that the temperature did not exceed 85° F. A single charge of granular trichloroisocyanuric acid (55 g) was then added to the reaction flask. Shortly after half of the TCCA was added, the bromine fumes in the flask were observed to subside. Compared to the process employing twice as much NaBr there were virtually no bromine vapors evident. It was not necessary to quell the fumes by addition of 50% NaOH prior to filtration. After about 20 minutes of stirring, all of the coarse TCCA granules were observed to have reacted as a fine powdery precipitate developed. Upon filtration of the insolubles, the filtercake was washed with 2 bed volumes of deionized water. The wash liquors were discarded, and the filter wetcake was placed in an oven to dry overnight at 130° F. To the filtrate was added additional 50% NaOH (95 g) again with cooling and stirring, and at a rate such that the temperature of the reaction did not exceed 80-90° F. Any additional solids that precipitated from solution were removed by vacuum filtration, immediately upon completing the addition of the 50% NaOH. Iodometric titration of the resultant golden solution yielded a total halogen content of 21.1% when expressed as $Br_2$ (or 9.4% when expressed as $Cl_2$). The theoretical amount of $Br_2$ and $Cl_2$ equivalent produced as a function of the amount of the TCCA charge was used to compute a reaction yield of 92.0%.

The Fourth Embodiment

This embodiment is a method of preparing heretofore unknown, highly water soluble, bromine-containing solid compositions of matter, namely, the alkali metal or earth alkali metal salt of hydrated N-bromosulfamate and the alkali metal or earth alkali metal salt of anhydrous N-bromosulfamate. The method uses anhydrous hydrogen bromide or aqueous hydrogen bromide precursors under reaction conditions designed to promote the formation of the solid, e.g. above the solubility limit.

A unique aspect of this method is that it can be used to yield three different useful products. The first is the solid alkali metal or earth alkali metal salt of hydrated N-bromosulfamate in equilibrium with its saturated solution. The solid need not be isolated from the saturated solution. Instead, the combination product, a slurry, may be advantageously packaged and transported to a separate location for subsequent reconstitution by simple addition of water to yield an aqueous stabilized, liquid bromine composition whose concentration can be tailored to the amount of reconstitution water used. The second and third products are the solid alkali metal or earth alkali metal salt of hydrated N-bromosulfamate and the solid alkali metal or earth alkali metal salt of anhydrous N-bromosulfamate, respectively. These high-activity solids are stable and dissolve rapidly and completely to yield a highly concentrated bromine containing solution.

The method preferably includes the following steps. Steps (a), (b), and (c) may be performed in any order, or simultaneously, followed by other steps as discussed below depending on whether the desired product is the slurry of the hydrated solid in equilibrium with its saturated solution or one of the two isolated solid products.

a. Utilizing a bromine compound in the oxidation state of −1.

Anhydrous hydrogen bromide gas or aqueous hydrogen bromide may be used. Typically, anhydrous hydrogen bromide gas is emitted from a reactor where bromination of an organic compound to form a brominated flame retardant is taking place. Aqueous hydrogen bromide is a preferred starting reagent and can be used at any concentration up to 70% by weight, but 48% is especially convenient to use as this is the concentration at which the product does not appreciably fume HBr vapors. When aqueous hydrogen bromide is the starting reagent, the process of this invention is conducted under conditions of extreme acidity, preferably at a pH which is greater than about −1 and less than about +1.

b. Introducing to the reaction medium a highly concentrated solution of hydrogen peroxide to effect a full or partial oxidation of the Br moieties into bromine.

$$2HBr + H_2O_2 \rightarrow Br_2 + 2H_2O \tag{42}$$

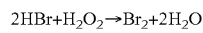

Strong solutions of hydrogen peroxide are preferably introduced to anhydrous hydrogen bromide or 48% aqueous hydrogen bromide solution, although this order of addition can be changed without appreciably effecting the reaction. Hydrogen peroxide is commercially available at concentrations up to 90%, although 50% hydrogen peroxide is safer to use and is more commonly available. When an all-aqueous reaction medium is preferred, 50% hydrogen peroxide is added slowly and with stirring to a solution of 48% aqueous hydrogen bromide calculated to have a pH of about −0.78. When a gas-liquid reaction medium is preferred, anhydrous hydrogen bromide gas is bubbled through a solution of 50% hydrogen peroxide. In either case, the amount of 50% hydrogen peroxide used should be sufficient to oxidize between 10% and 100% of the stoichiometric amount, and most preferably between 20% and 80% of the stoichiometric amount of the Br moieties into bromine. The oxidation of anhydrous hydrogen bromide gas or aqueous 48% aqueous hydrogen bromide with 50% hydrogen peroxide is an exothermic reaction. Heat removal is effected by conducting the reaction at the refluxing temperature of the reaction mixture using a condenser to facilitate the heat removal process. Alternatively, cooling is effected with a jacketed reactor. The reaction time and temperature are controlled in order to maximize the conversion of Br moieties into bromine and minimize the amount of unreacted hydrogen peroxide remaining in the reaction medium.

c. Mixing a complexing agent to the fully or partially oxidized solution.

On allowing the highly acidic, bromine-laden reaction mixture to cool, a complexing agent is introduced to the same reactor. Preferably the complexing agent is sulfamic acid. The amount of sulfamic acid added depends on the amount of anhydrous hydrogen bromide or aqueous hydrogen bromide originally present. A mole ratio of about 0.75:1 to about 1.5:1 sulfamic acid to Br moiety is advantageous to the stability of the final product with about 0.95:1 to about 1.2:1 being the most preferred mole ratio range.

In the event that the reaction medium is 100% oxidized by hydrogen peroxide in step (b), steps (d)-(f) are not performed and the method continues with step (g) with subsequent steps depending on whether the desired product is the slurry of the hydrated solid in equilibrium with its saturated solution or one of the two isolated solid products. In the event that the reaction medium is only partially oxidized in step (b), steps (d)-(f) are performed, followed by step (g) and subsequent steps depending on whether the desired product is the slurry of the hydrated solid in equilibrium with its saturated solution or one of the two isolated solid products.

The next step is either (d) or (e).

d. Adding a solid alkaline source to the reaction medium to adjust its pH to between about 0.5 and about 9 and preferably between about 1.0 and about 4.5, followed by introducing sufficient solid organic halogenating agent to oxidize all or substantially all of the remaining bromide ions into bromine.

Any solid alkaline source may be employed. Examples include, but are not limited to, alkali metal or earth alkali metal carbonates, bicarbonates, oxides, and hydroxides. A particularly preferred solid alkaline source is NaOH. The solid sodium hydroxide is introduced to the reaction medium slowly, and with stirring and cooling such that the temperature preferably does not exceed 80° F.

Solid organic halogenating agents include any organic compound in which one or more halogen atoms such as Cl, Br, or I is present in the oxidation state of +1 and is covalently bound to a nitrogen or phosphorus atom within the same molecule. Suitable examples include, but are not limited to, trichloroisocyanuric acid (TCCA), sodium dichlorisocyanurate (NaDCC), sodium dichlorisocyanurate dihydrate (NaDCC.2H$_2$O), trichloromelamine, N-chloro-p-toluenesulfonamide, N-chloromethanesulfonamide, N-chlorosuccinimide, N,N'-1,3-bromochloro-5,5-dimethylhydantoin, N,N'-1,3-bromochloro-5-ethyl-5-methylhydantoin, 1,3-dibromo-5,5-dimethylhydantoin, 1,3-dichloro-5,5-dimethylhydantoin, and N-bromosuccinimide.

A particularly preferred source of a solid, organic halogenating agent is trichloroisocyanuric acid (TCCA), which reacts according to the following equation:

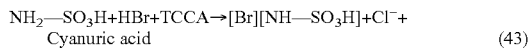

(43)

Preferably this is used in the form of a coarse granular grade of material for ease of introduction to the stirred, cooled reactor. As the TCCA reacts, the coarse granules disappear. The reaction is considered to be complete when no more coarse granules are evident. Although dry, granular TCCA is favored because of its easy handling characteristics, and for providing a visual signal that the reaction is complete, TCCA powdered wetcake may also be employed. The advantage of using TCCA wetcake is that it may be taken directly from the TCCA-producing reactors and so costs associated with drying and granulation of the material are eliminated.

If step (d) is used, step (e) is not used. If step (d) is not used, step (e) is used.

e. Adding a solid alkaline source to the reaction mother liquors such that if the alkaline source is a hydroxide salt, the overall mole ratio of bromine compound in the oxidation state of −1 to hydroxide is between about 0.5:1 and about 1:2, preferably between about 1:1, followed by introducing sufficient solid inorganic halogenating agent to oxidize all or substantially all of the remaining bromide ions into bromine.

Any solid alkaline source may be employed. Examples include, but are not limited to, alkali metal or earth alkali metal carbonates, bicarbonates, oxides, and hydroxides. A particularly preferred solid alkaline source is NaOH. The solid sodium hydroxide is introduced to the reaction medium slowly, and with stirring and cooling such that the temperature preferably does not exceed 80° F.

Solid inorganic halogenating agents include, but are not limited to, alkali metal and earth alkali metal hypochlorite salts. Suitable examples include lithium hypochlorite, calcium hypochlorite, and magnesium hypochlorite. Due to its low cost and high available chlorine content, calcium hypochlorite is particularly preferred. The higher strength granular forms of the product (containing 65-75% available chlorine) are most preferred.

Under acidic conditions (pH between about −1 and about 5), the oxidation reaction is virtually instantaneous, and proceeds to completion in a short time. The calcium hypochlorite is preferably added rapidly and with good mixing in order to minimize loss of bromine vapors from the reaction medium, but not too quickly such that that phase separation of elemental bromine becomes apparent at the bottom of the reactor. When the addition of the solid calcium hypochlorite is complete, all the sulfamic acid has solubilized to yield an acidic reaction medium. Preferably the calcium hypochlorite is used in the form of a coarse granular grade of material for ease of introduction to the stirred, cooled reactor. As the calcium hypochlorite reacts, the coarse granules disappear. The reaction is considered to be complete when no more coarse granules are evident.

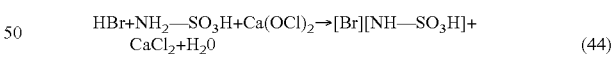

(44)

f. Removing any insoluble reaction by-products with a conventional solid-liquid separation technique.

Any suitable solid-liquid separation technique can be employed. Suitable examples include, but are not limited to, centrifugation, clarification, gravity sedimentation, and vacuum filtration. Filtration is a particularly preferred technique for effecting solid-liquid separation.

When the solid organic halogenating agent is TCCA, cyanuric acid is a reaction by-product that is insoluble in the reaction medium (see reaction (43)). Filtration of the cyanuric acid (CA) residue is carried out at pH 1-9, but preferably at about pH 1-6 to maximize CA recovery from solution and minimize the amount of bromine that fumes from the reaction medium. Upon washing the filtercake with water to remove the mother liquors, a highly pure CA wetcake is recovered. This can be recycled to other processes to make additional quantities of TCCA, NaDCC, or NaDCC.2H$_2$O that can be used in the method of the current invention.

If desired, this step can be modified so that the sodium salt of cyanuric acid is recovered from the reaction medium instead of cyanuric acid. This is accomplished by introducing, before performing the solid-liquid separation, sufficient solid NaOH to react with cyanuric acid according to the following equation:

$$CA+NaOH \rightarrow NaCA+H_2O \tag{45}$$

The amount of solid sodium hydroxide solution employed depends on the amount of solid organic halogenating agent used in step (d). When TCCA is the solid organic halogenating agent, sufficient solid NaOH is introduced slowly with mixing and cooling to convert all or substantially all of the cyanuric acid liberated in reaction (43) into its monosodium salt via reaction (45). Monosodium cyanurate is insoluble in the reaction medium at pH<9. As is true of cyanuric acid, monosodium cyanurate can be separated and recycled to other processes in order to make additional quantities of TCCA, NaDCC, or NaDCC.2H$_2$O that can be used in the method of the current invention. This is accomplished by performing a solid-liquid separation, as described above, which is done when the pH stabilizes at about 9.

When the solid inorganic halogenating agent is calcium hypochlorite, insoluble reaction by-products include calcium carbonate, lime, and quicklime. Filtration of the reaction medium is carried out at pH 1-9, but preferably at about pH 4-8 to reduce the problem of CO$_2$ gas being liberated from calcium carbonate and also minimize the amount of bromine that fumes from the reaction medium.

g. Adding a solid alkaline source to the reaction mother liquors such that if the alkaline source is a hydroxide salt, the overall mole ratio of bromine compound in the oxidation state of −1 to hydroxide is between about 1:2 and about 1:5; preferably between about 1:3 and about 1:4. This does not include any hydroxide salt that may be used to convert cyanuric acid into its alkali metal or earth alkali metal salt as described in step (f).

Any solid alkaline source may be employed. Examples include, but are not limited to, alkali metal or earth alkali metal carbonates, bicarbonates, oxides, and hydroxides. A particularly preferred source of alkali metal or earth alkali metal hydroxide is solid NaOH. The sodium hydroxide is introduced to the reaction medium slowly, and with stirring and cooling such that the temperature preferably does not exceed 80° F. The purpose is to deprotonate the bromo derivative of sulfamic acid to form the bromo derivative of sodium sulfamate according to reaction (46).

$$[Br][NH-SO_3H]+NaOH \rightarrow [Br][NH-SO_3^-][Na^+]+H_2O \tag{46}$$

The amount of NaOH employed depends on the initial charge of bromine compound in the oxidation state of −1. The overall mole ratio of bromine compound in the oxidation state of −1 to NaOH added in steps (d) or (e), if performed, and (g) is in the range of about 1:2 to about 1:5, preferably about 1:3 to about 1:4. This does not include any hydroxide salt that may be used to convert cyanuric acid into its monosodium salt as described in step (f).

h. Removing any further insoluble reaction by-products that develop with a conventional solid-liquid separation technique.

As noted above, any suitable solid-liquid separation technique may be employed. Generally, when TCCA is the halogenating agent, almost 90% of CA reaction by-product is recovered as a highly pure wetcake in the first solid-liquid separation operation described in step (f). While not wishing to be bound by theory, it is believed that salts of cyanuric acid are precipitated from the reaction mother liquors upon the addition of alkaline sources. When the alkaline source is, for example, solid sodium hydroxide, the mono-, di-, and trisodium salts of cyanuric acid are precipitated. Although insoluble in the reaction mother liquors, the di and trisodium salts display exceptional solubility in ordinary water and are thus useful water treating agents in their own right. However, in comparison to the amount of solids recovered in step (f), the amount of solid that may subsequently develop is relatively low and step (h) may require only a polishing solid-liquid separation, with, for example, a cartridge filter. Moreover, the two solid-liquid separation steps of (f) and (h) may be combined into a single operation performed only at step (f).

i. Chilling, seeding, evaporating, or otherwise promoting crystallization of the bromine-containing salt from its supersaturated solution.

Crystallization of the bromine-containing solid from its supersaturated solution may be achieved by any conventional means. These methods include, but are not limited to, chilling the reaction medium to reduce the solubility of the bromine-containing salt even further to trigger the precipitation process, seeding the reaction medium with bromine-containing salts obtained in an earlier crop so as to provide a surface on which additional crystals are encouraged to nucleate and grow, and evaporating the reaction medium under vacuum to drive off solvent water and promote the crystallization process.

In certain situations, it may be desirable to conclude the method at this point and leave the alkali metal or earth alkali metal salt of hydrated N-bromosulfamate in equilibrium with its saturated solution. This combination product, a slurry, may be advantageously packaged and transported to a separate location for subsequent reconstitution by simple addition of water to yield an aqueous stabilized liquid bromine-containing composition whose concentration can be tailored to the amount of reconstitution water used.

j. Recovering the resultant solid alkali metal or earth alkali metal salt of hydrated N-bromosulfamate.

Any suitable solid-liquid separation technique can be employed to separate crystals of the alkali metal or earth alkali metal salt of hydrated N-bromosulfamate from the reaction mother liquors. Suitable examples include, but are not limited to, centrifugation, clarification, gravity sedimentation, and vacuum filtration. Filtration is a particularly preferred technique for effecting solid-liquid separation. The solid recovered is the alkali metal or earth alkali metal salt of hydrated N-bromosulfamate as a crystalline material.

In order to obtain the alkali metal or earth alkali metal salt of anhydrous N-bromosulfamate, the hydrated solid must be dried. Any suitable drying technique may be employed to dry the solid. Suitable examples include, but are not limited to, fluidized bed drying, vacuum oven drying, flash drying, and drying over dessicant, such as molecular sieves. Upon dehydration, the solid that is recovered is the alkali metal or earth alkali metal salt of anhydrous N-bromosulfamate.

Example 16

To a stirred reaction flask containing 48% HBr (69.5 g) was added 50% H$_2$O$_2$ (10.6 g) dropwise so that the reaction flask temperature did not exceed 142° F. After allowing the reaction flask to cool to about 90° F., solid sulfamic acid (48 g) was introduced. The resulting slurry was stirred as solid sodium hydroxide pellets were charged to the reaction flask.

The flask was chilled during this process so that the temperature did not exceed 80° F. A single charge of granular trichloroisocyanuric acid (22.0 g) was introduced to the reaction flask that was stirred for about 20 minutes. Not all the coarse TCCA granules were observed to have reacted during this time, and so deionized water (5 ml) was added to the reactor to assist the process. As the reaction proceeded, a fine powdery precipitate developed which was removed by vacuum filtration. Then additional solid NaOH pellets (17 g) were introduced also with cooling and at a rate such that the temperature did not exceed 80° F. Any additional precipitate that developed was immediately removed by vacuum filtration. Iodometric titration of the resulting golden yellow solution was used to determine its $Br_2$ content of 27.2% (or 12.1% as $Cl_2$). Within a few minutes, this highly concentrated bromine solution started to turn turbid as crystals began to form. The crystallizing solution was chilled in an ice bath to expedite the development of the crystals. A large crop of yellow crystalline material was separated by vacuum filtration, and the mother liquors were retitrated iodometrically. The new bromine content was found to be 24.3% (10.8% as $Cl_2$), indicating that the solution had lost soluble oxidant as the solids crystallized. The yellow crystalline material displayed exceptionally high solubility in water. The dissolution process was rapid and complete. There were no insoluble residues. Iodometric titration of resulting solutions was used to calculate that the crystalline solid contained 29.9% $Br_2$ (13.1% as $Cl_2$).

The Fifth Embodiment

The fifth embodiment is a method of producing heretofore unknown, highly water soluble, bromine-containing solid compositions of matter, namely, the alkali metal or earth alkali metal salt of hydrated N-bromosulfamate and the alkali metal or earth alkali metal salt of anhydrous N-bromosulfamate. The method uses alkali metal or earth alkali metal bromide ion solutions under reaction conditions designed to promote the formation of the solid, e.g. above the solubility limit.

A unique aspect of this method is that it can be used to yield three different useful products. The first is the solid alkali metal or earth alkali metal salt of hydrated N-bromosulfamate in equilibrium with its saturated solution. The solid need not be isolated from the saturated solution. Instead, the combination product, a slurry, may be advantageously packaged and transported to a separate location for subsequent reconstitution by simple addition of water to yield an aqueous stabilized, liquid bromine composition whose concentration can be tailored to the amount of reconstitution water used. The second and third products are the solid alkali metal or earth alkali metal salt of hydrated N-bromosulfamate and the solid alkali metal or earth alkali metal salt of anhydrous N-bromosulfamate, respectively. These high-activity solids are stable and dissolve rapidly and completely to yield a highly concentrated bromine containing solution.

The method preferably includes the following steps. Steps (a), (b), and (c) may be performed in any order, or simultaneously, followed by other steps depending on whether the desired product is the slurry of hydrated solid in equilibrium with its saturated solution or one of the two isolated solid products.

a. Utilizing an alkali metal or earth alkali metal solution of bromide ions.

Sources of alkali metal or earth alkali metal solutions of bromide ion include, but are not limited to, lithium bromide, sodium bromide, potassium bromide, calcium bromide, and magnesium bromide. A preferred source of bromide ion solution is sodium bromide solution, commonly available as a 40-46% aqueous solution, or it may be made into such a solution by dissolving solid sodium bromide salt in water.

b. Mixing a complexing agent to the bromide ion solution.

Preferably, the complexing agent is sulfamic acid. The amount of sulfamic acid added depends on the amount of bromide ion originally present. A mole ratio of about 0.75:1 to about 1.5:1 sulfamic acid to sodium is advantageous to the stability of the final product, with about 0.95:1 to about 1.2:1 being the most preferred mole ratio range.

c. Adding an alkaline source to the reaction medium to adjust its pH to between about 0.5 and about 9 and preferably between about 1.0 and about 4.5, followed by introducing sufficient solid, organic halogenating agent to oxidize all or substantially all of the bromide ions into bromine.

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted with water and used in the process of this invention. The sodium hydroxide solution is introduced to the reaction medium slowly, and with stirring and cooling such that the temperature preferably does not exceed 80° F.

Solid organic halogenating agents include any organic compound in which one or more halogen atoms such as Cl, Br, or I is present in the oxidation state of +1 and is covalently bound to a nitrogen or phosphorus atom within the same molecule. Suitable examples include, but are not limited to, trichloroisocyanuric acid (TCCA), sodium dichlorisocyanurate (NaDCC), sodium dichlorisocyanurate dihydrate (NaDCC.2$H_2O$), trichloromelamine, N-chloro-p-toluenesulfonamide, N-chloromethanesulfonamide, N-chlorosuccinimide, N,N'-1,3-bromochloro-5,5-dimethylhydantoin, N,N'-1,3-bromochloro-5-ethyl-5-methylhydantoin, 1,3-dibromo-5,5-dimethylhydantoin, 1,3-dichloro-5,5-dimethylhydantoin, and N-bromosuccinimide. A particularly preferred source of a solid, organic halogenating agent is trichloroisocyanuric acid (TCCA). Preferably this is used in the form of a coarse granular grade of material for ease of introduction to the stirred, cooled reactor. As the TCCA reacts, the coarse granules disappear. The reaction is considered to be complete when no more coarse granules are evident. Although dry, granular TCCA is favored because of its easy handling characteristics and for providing a visual signal that the reaction is complete, TCCA powdered wetcake may also be employed. The advantage of using TCCA wetcake is that it may be taken directly from the TCCA-producing reactors, and so costs associated with drying and granulation of the material are eliminated.

$$NaBr+NaOH+NH_2-SO_3H+TCCA \rightarrow [Br][NH-SO_3H]+NaCl+H_2O+\text{Cyanuric Acid} \quad (47)$$

d. Removing any insoluble reaction by-products with a conventional solid-liquid separation technique.

Any suitable solid-liquid separation technique can be employed. Suitable examples include, but are not limited to, centrifugation, clarification, gravity sedimentation, and vacuum filtration. Filtration is a particularly preferred technique for effecting solid-liquid separation.

When the solid organic halogenating agent is TCCA, cyanuric acid is a reaction by-product that is insoluble in the reaction medium. Filtration of the cyanuric acid (CA) residue is carried out at pH 1-9, but preferably at about pH 1-6 to maximize CA recovery from solution and minimize the amount of bromine that fumes from the reaction medium (see reaction (44)). Upon washing the filtercake with water to remove the mother liquors, a highly pure CA wetcake is recovered. This can be recycled to other processes to make additional quantities of TCCA, NaDCC, or NaDCC.2H$_2$O that can be used in the method of the current invention.

If desired, this step can be modified so that the sodium salt of cyanuric acid is recovered from the reaction medium instead of cyanuric acid. This is accomplished by introducing, before performing the solid-liquid separation, sufficient 50% NaOH solution to react with cyanuric acid according to the following equation:

$$CA + NaOH \rightarrow NaCA + H_2O \quad (48)$$

The amount of 50% sodium hydroxide solution employed depends on the amount of solid organic halogenating agent used in step (c). When TCCA is the solid organic halogenating agent, sufficient 50% NaOH solution is introduced slowly with mixing and cooling to convert all or substantially all of the cyanuric acid liberated in reaction (47) into its monosodium salt via reaction (48). Monosodium cyanurate is insoluble in the reaction medium at pH<9. As is true of cyanuric acid, monosodium cyanurate can be separated and recycled to other processes in order to make additional quantities of TCCA, NaDCC, or NaDCC.2H$_2$O that can be used in the method of the current invention. This is accomplished by performing a solid-liquid separation, as described above, which is done when the pH stabilizes at about 9.

e. Adding an alkaline source to the reaction mother liquors such that if the alkaline source is a hydroxide salt, the overall mole ratio of aqueous alkali metal or earth alkali metal bromide to hydroxide is between about 1:2 and about 1:5, preferably between about 1:3 and 1:4. This does not include any hydroxide salt that may be used to convert cyanuric acid into its alkali metal or earth alkali metal salt as described in step (d).

Any alkaline source may be employed. Examples include, but are not limited to, alkali metal or earth alkali metal carbonates, bicarbonates, oxides, and hydroxides. When solutions are preferred, sodium hydroxide or potassium hydroxide solutions are convenient to use, alone or in combination with each other. A particularly preferred alkaline source is 50% NaOH solution. To prevent storage problems in cold climates, 50% NaOH solution may be diluted to 25% and used. The sodium hydroxide solution is introduced to the reaction medium slowly, and with stirring and cooling such that the temperature preferably does not exceed 80° F. The purpose is to deprotonate the bromo derivative of sulfamic acid to form the bromo derivative of sodium sulfamate according to reaction (49).

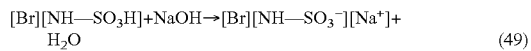
$$[Br][NH-SO_3H] + NaOH \rightarrow [Br][NH-SO_3^-][Na^+] + H_2O \quad (49)$$

The amount of 50% NaOH solution employed depends on the initial charge of aqueous alkali metal or earth alkali metal bromide. The overall mole ratio of aqueous alkali metal or earth alkali metal bromide to NaOH added in steps (c) and (e) is in the range of about 1:2 to about 1:5, preferably about 1:3 to about 1:4. This does not include any hydroxide salt that may be used to convert cyanuric acid into its monosodium salt as described in step (d).

f. Removing any further insoluble reaction by-products that develop with a conventional solid-liquid separation technique.

As noted above, any suitable solid-liquid separation technique may be employed. Generally, when TCCA is the halogenating agent, almost 90% of CA reaction by-product is recovered as a highly pure wetcake in the first solid-liquid separation operation described in step (d). While not wishing to be bound by theory, it is believed that salts of cyanuric acid are precipitated from the reaction mother liquors upon the addition of alkaline sources. When the alkaline source is, for example, 50% sodium hydroxide solution, the mono-, di-, and trisodium salts of cyanuric acid are precipitated. Although insoluble in the reaction mother liquors, the di and trisodium salts display exceptional solubility in ordinary water and are thus useful water treating agents in their own right. However, in comparison to the amount of solids recovered in step (d), the amount of solid that may subsequently develop is relatively low and step (f) may require only a polishing solid-liquid separation, with, for example, a cartridge filter. Moreover, the two solid-liquid separation steps of (d) and (f) may be combined into a single operation performed only at step (d).

g. Chilling, seeding, evaporating, or otherwise promoting crystallization of the bromine-containing salt from its supersaturated solution.

Crystallization of the bromine-containing solid from its supersaturated solution may be achieved by any conventional means. These methods include, but are not limited to, chilling the reaction medium to reduce the solubility of the bromine-containing salt even further to trigger the precipitation process, seeding the reaction medium with bromine-containing salts obtained in an earlier crop so as to provide a surface on which additional crystals are encouraged to nucleate and grow, and evaporating the reaction medium under vacuum to drive off solvent water and promote the crystallization process.

In certain situations, it may be desirable to conclude the method at this point and leave the alkali metal or earth alkali metal salt of hydrated N-bromosulfamate in equilibrium with its saturated solution. This combination product, a slurry, may be advantageously packaged and transported to a separate location for subsequent reconstitution by simple addition of water to yield an aqueous stabilized liquid bromine-containing composition whose concentration can be tailored to the amount of reconstitution water used.

h. Recovering the resultant solid alkali metal or earth alkali metal salt of hydrated N-bromosulfamate.

Any suitable solid-liquid separation technique can be employed to separate crystals of alkali metal or earth alkali metal salt of hydrated N-bromosulfamate from the reaction mother liquors. Suitable examples include, but are not limited to, centrifugation, clarification, gravity sedimentation, and vacuum filtration. Filtration is a particularly preferred technique for effecting solid-liquid separation. The solid recovered is the alkali metal or earth alkali metal salt of hydrated N-bromosulfamate as a crystalline material.

In order to obtain the alkali metal or earth alkali metal salt of anhydrous N-bromosulfamate, the hydrated salt must be dried. Any suitable drying technique can be employed to dry the solid. Suitable examples include, but are not limited to, fluidized bed drying, vacuum oven drying, flash drying, and drying over dessicant, such as molecular sieves. The solid that is recovered is the alkali metal or earth alkali metal salt of anhydrous N-bromosulfamate.

Example 17

To a stirred reaction flask containing 40% sodium bromide solution was added solid sulfamic acid (82.3 g). The resultant slurry was stirred as 50% sodium hydroxide (60.2 g) was introduced. The flask was chilled during this process so that the temperature did not exceed 80° F. A single charge of trichlorocyanuric acid (55 g) was then introduced to the stirred reaction flask. However, the reaction medium became very viscous, and this hampered the mixing efficiency, so deionized water (35.8 g) was added to thin the mixture. The fine powdery precipitate that developed was removed by vacuum filtration. Then, 50% NaOH solution (100 g) was added also with cooling and at such a rate that the temperature did not exceed 80° F. Any additional solid that developed during this addition process was immediately removed by vacuum filtration. Iodometric titration of the resulting golden yellow solution was used to determine its bromine content of 22.7% as $Br_2$ (10.1% as $Cl_2$) which corresponded to 100% yield. On standing for two days in a cool environment, a single, large crystalline mass weighing 33 g had developed. The mother liquors were determined to have a bromine content of 20.9% as $Br_2$ (9.3% as $Cl_2$) by iodometric titration. The crystalline mass was observed to comprise mainly regular rhombohedral crystals, possessing a yellow glass-like appearance. A section of the crystalline mass was dissolved in water. It dissolved rapidly and completely. Iodometric titration of the solution was used to calculate that the crystalline solid contained 47.2% as $Br_2$ (21% as $Cl_2$).

The Sixth Embodiment

The sixth embodiment of this invention is a stable, liquid composition of matter that contains 60-80% more available bromine than the two products that are currently available. One product, described in U.S. Pat. Nos. 5,683,654, 5,795,487, 5,942,126, and 6,136,205, is prepared from a process using sodium hypochlorite solution. It is reported to contain 14% as $Br_2$ (6.3% as $Cl_2$). The other product, described in U.S. Pat. Nos. 6,068,861, 6,495,169, and 6,322,822, is prepared from a process using bromine chloride. It is reported to contain 15.5% as $Br_2$ (6.9% as $Cl_2$). Further, U.S. Pat. Nos. 6,299,909, 6,306,441, and 6,348,219 disclose an upper ceiling of 18% as $Br_2$ (8% as $Cl_2$) as the highest strength concentrate that could be made by the bromine chloride process. The composition of the sixth embodiment is low in dissolved halide ion salts, permitting it to contain greater than about 18% as $Br_2$ (8% as $Cl_2$) and still maintain excellent physical and chemical stability. This composition may be prepared using the methods of the first, second, and third embodiments of the invention.

The bromine-containing aqueous composition has the following attributes and advantages:

(1) It has an active ingredient content of at least about 18% as $Br_2$ (8% as $Cl_2$);
(2) It is prepared to contain between zero and about 1 mole of dissolved halide ion salts per mole of active halogen (expressed as $Br_2$ or $Cl_2$);
(3) It has an active ingredient content in which most of the halogen is present as bromine;
(4) It has chemical stability with an active ingredient half-life of at least about 58 days at about 125° F.;
(5) It has physical stability as being devoid of solid precipitates, nor strongly prone to the development of solid precipitates on storage;
(6) It has physical stability to at least about three cycles of freezing and thawing; and
(7) It has an undetectable level of bromate ion.

None of the previously reported solutions exhibits all of these attributes. None of the previously reported commercially available solutions has an active ingredient content as high as 18% as $Br_2$ (8% as $Cl_2$). All of the commercially available solutions, when prepared, have at least 1-2 moles of dissolved halide ion salts per mole of active halogen (expressed as $Br_2$ or $Cl_2$).

Example 18

The chemical and physical stability of the aqueous bromine solutions were assessed at elevated temperatures. Samples were poured into capped plastic containers and placed in an oven held between 120-130° F. The chemical stability was determined by measuring the amount of active ingredient remaining in the formulation as a function of time. The physical stability was established by visual observation of whether any solids precipitated from solution over the same period and were evident on the side or bottom of the container, or floating on the surface of the solution. The data in Table V shows the chemical and physical stability of a sample prepared according to Example 5 described earlier.

TABLE V

| Day | Chemical Stability of Active Ingredient | | Physical Stability |
| --- | --- | --- | --- |
|  | Wt. % $Cl_2$ | % Remaining | Precipitation? |
| 0 | 10.83 | 100 | None |
| 26 | 8.61 | 79.5 | None |
| 30 | 8.41 | 77.6 | None |
| 37 | 8.25 | 76.2 | None |
| 44 | 7.67 | 70.8 | None |
| 54 | 7.33 | 67.6 | Slight |
| 58 | 7.01 | 64.7 | Slight |

Example 19

The freeze-thaw cyclability of the aqueous bromine concentrate prepared in Example 5 was assessed by freezing a sample in the freezer compartment of a refrigerator followed by thawing. The temperature of the frozen composition was recorded immediately upon removing it from the freezer (the chill temperature). As the sample thawed, the temperature at which the last crystal to disappear was measured. Table VI summarizes the observations.

TABLE VI

| Cycle Number | Chill Temperature/° F. | Last Crystal to Disappear/° F. |
| --- | --- | --- |
| 1 | 13.4 | 49 |
| 2 | 23.8 | 49.6 |
| 3 | 2.1 | 130 |

Example 20

The biocidal performance of the liquid composition of the present invention was compared to a solution of sodium bromide activated using an equimolar amount of sodium hypochlorite bleach, and a solution prepared from 1-bromo-3-chloro-5,5-dimethylhydantoin (BCDMH). Sterile phosphate buffer samples (pH 8.5) were inoculated with *Pseudomonas aeruginosa* to give a concentration of approximately $5\times10^6$ bacteria/ml and then challenged with the test systems at a nominal concentration of 0.2 ppm total halogen (as $Cl_2$).

After a contact time of 10 minutes at 35° C., an aliquot of sodium thiosulfate was added to each sample to neutralize the halogen. The level of viable bacteria in each sample was determined by plate counting. Plates were incubated at 35° C. for 48 hours. The results expressed as log reduction in viable bacteria/ml are summarized in Table VII below.

TABLE VII

| Test Sample | Nominal dose of total halogen/ ppm as $Cl_2$ | Measured dose of total halogen/ ppm as $Cl_2$ | Viable bacteria/ ml after 10 minutes | Log Reduction |
|---|---|---|---|---|
| Control | — | — | $5.3 \times 10^6$ | — |
| Present invention | 0.2 | 0.19 | $2.5 \times 10^3$ | 3.3 |
| NaBr/NaOCl | 0.2 | 0.14 | $2.1 \times 10^2$ | 4.4 |
| BCDMH | 0.2 | 0.17 | $2.5 \times 10^3$ | 3.3 |

Thus, the biocidal performance of the liquid composition of the present invention was comparable to that of other bromine-based biocides.

Example 21

Anion chromatography was used to measure the amount of bromate ion present in the solutions of the present invention. A sample that had been prepared 32 days earlier was analyzed using the technique. Bromate was measured at less than 50 ppm, which is below the detection limit of the method. Thus, bromate is not formed in the reaction process, nor is it formed as the sample ages.

The Seventh Embodiment

The seventh embodiment of this invention is a stable, liquid mixed halogen composition that contains both bromine and chlorine. Typically, the composition is low in dissolved halide ion salts, permitting it to contain a total halogen level greater than 21% when expressed as $Br_2$ (9.4% when expressed as $Cl_2$). The composition may, however, contain a total halogen level as low as 2.25% when expressed as $Br_2$ (1% when expressed as $Cl_2$). The ratio of bromine to chlorine in the composition can vary. A useful mixed halogen composition may contain 50 mole % bromine: 50 mole % chlorine and up to 90 mole % bromine: 10 mole % chlorine. The mixed halogen composition may be prepared using the methods of the second and third embodiments of the invention.

The mixed halogen composition has the following attributes and advantages:

(1) It has a total halogen content of at least 2.25% when expressed as $Br_2$ (1% when expressed as $Cl_2$);
(2) It has between zero and less than 1 mole of dissolved halide ion salts per mole of active halogen (expressed as $Br_2$ or $Cl_2$);
(3) It has an active ingredient content in which the halogen is present as both bromine and chlorine;
(4) A 50 mole % bromine: 50 mole % chlorine mixed halogen composition with a total halogen content of 21% when expressed as $Br_2$ (9.4% when expressed as $Cl_2$) has a chemical stability such that more than 90% of the active ingredient remains after 34 days storage at 120° F.;
(5) It has physical stability as being devoid of solid precipitates, nor strongly prone to the development of solid precipitates; and
(6) It has an undetectable level of bromate ion.

Example 22

The chemical stability of the mixed halogen solution prepared in Example 15 was assessed at ambient and elevated temperatures. The sample was poured into a capped plastic container and placed in an oven held at 120° F. The amount of active ingredient remaining in the composition was monitored as a function of time. The physical stability was established by visual observation of whether any solids precipitated from solution over the same period and were evident on the side or bottom of the container, or floating on the surface of the solution. The data in Table VIII shows the results. It can be seen that even after one month at 120° F., less than 10% of the halogen has been depleted and there was no evidence of solids formation in either the ambient temperature or 120° F. samples.

TABLE VIII

| | Ambient Temperature | | | 120° F. | | |
|---|---|---|---|---|---|---|
| Day | Solids Formed? | Wt. % $Cl_2$ | % Remaining | Wt. % $Cl_2$ | % Remaining | Solids Formed? |
| 0 | No | 9.39 | 100 | 9.39 | 100 | No |
| 12 | No | 9.21 | 98.1 | 8.8 | 93.7 | No |
| 19 | No | 9.07 | 96.6 | 8.65 | 92.1 | No |
| 34 | No | 9.15 | 97.4 | 8.56 | 91.1 | No |

The Eighth Embodiment

The eighth embodiment of this invention is two bromine-containing solid compositions of matter: (1) the alkali metal or earth alkali metal salt of hydrated N-bromosulfamate; and (2) the alkali metal or earth alkali metal salt of anhydrous N-bromosulfamate. These compositions may be prepared using the methods of the fourth and fifth embodiments of the invention.

The solid compositions have the following attributes and advantages:

(1) They dissolve quickly and completely in water to yield high-strength bromine-containing solutions;
(2) They can be applied directly to water in order to rapidly furnish that water with active bromine;
(3) The alkali metal or earth alkali metal salt of hydrated N-bromosulfamate is completely stable in equilibrium with its saturated solution such that the slurry may be advantageously packaged and transported to a separate location for subsequent reconstitution by the simple addition of water to yield an aqueous stabilized liquid bromine-containing composition whose concentration can be tailored to the amount of reconstitution water used; and
(4) The alkali metal or earth alkali metal salt of anhydrous N-bromosulfamate is extremely stable if kept dry and in vacuo (see Example 24). Therefore, the product may be advantageously packaged and transported to a separate location for subsequent reconstitution by the simple addition of water to yield an aqueous stabilized liquid bromine-containing composition whose concentration can be tailored to the amount of reconstitution water used.

Example 23

The crystals recovered from solution in Example 17 were manually dried of the reaction mother liquors with a paper towel. The crystals were glass-like, yellow, regular rhomohedra. Iodometric tiration to determine the oxidizing activity of the crystals meant dissolving some of the solid in water. They dissolved quickly and completely. The result of the titration revealed that the solid contained 23.6% active bromine (as Br).

A further portion of the towel-dried crystals was dissolved in water for analysis by atomic absorption spectroscopy. The data indicated that it contained 9.35% sodium ion.

A further portion of the towel-dried crystals recovered from Example 17 was weighed out and placed overnight in an oven set to 130° F. The yellow, glass-like, regular rhombohedral crystals had turned to a dull, yellow amorphous powder in the oven. Upon reweighing, a loss of 32% of the original weight was determined. Because the loss in weight was associated with a loss in crystallinity, most of the weight loss was attributed to the removal of water of crystallization molecules.

X-ray fluorescence spectroscopy on the crystals confirmed the presence of sodium, sulfur, and bromine atoms. This information, together with the bromine, sodium, and water content, indicated that the solid was the sodium salt of hydrated N-bromosulfamate designated by the formula $[Na^+][Br—NH—SO_3^-]\cdot nH_2O$.

Another large portion of the crystalline mass was dried with a paper towel and placed in a ceramic crucible that was heated on a hot plate. At about 221° F., the water of crystallization molecules were observed to boil from the product, which then decomposed and evolved dark red bromine vapors. A white residue was left behind, which was found to be extremely soluble in water.

X-ray diffraction spectroscopy on the crystals yielded a characteristic diffraction pattern. The responses due to likely contaminants associated with the solid (NaCl, NaOH, $Na_2SO_4$) were subtracted from the spectrum. The diffraction angle data (2 Theta) and the relative intensities of the responses are shown in Table IX.

TABLE IX

| 2 Theta/degrees | Intensity |
|---|---|
| 12.14 | 3189 |
| 14.52 | 1203 |
| 14.78 | 1181 |
| 16.00 | 588 |
| 16.36 | 524 |
| 16.54 | 743 |
| 16.76 | 1983 |
| 20.70 | 1988 |
| 24.34 | 3294 |
| 26.96 | 1170 |
| 27.68 | 1819 |
| 28.26 | 1524 |
| 28.52 | 3294 |
| 29.66 | 2912 |
| 30.28 | 948 |
| 36.76 | 1019 |
| 39.16 | 1031 |
| 39.26 | 654 |
| 41.94 | 548 |
| 43.96 | 633 |
| 45.52 | 841 |
| 45.82 | 315 |
| 46.00 | 531 |
| 46.18 | 900 |
| 48.14 | 545 |
| 50.78 | 454 |
| 52.50 | 295 |
| 52.90 | 344 |

Example 24

A further portion of the towel dried crystals from Example 17 was dehydrated by placing in a vacuum dessicator containing molecular sieves. After 15 days, a loss of 31% of the original weight was determined. Although the crystals lost their glass-like appearance, the rhombohedral shape was retained. The loss in weight was correlated with an increase in active ingredient content to 33.6% as Br. Hence, this solid is the sodium salt of anhydrous N-bromosulfamate designated by the formula $[Na^+][Br—NH—SO_3^-]$.

The sodium salt of anhydrous N-bromosulfamate was placed back in the vacuum dessicator. After three months of storage at room temperature, it was re-analyzed and determined not to have lost any activity.

The invention has been described above with reference to the preferred embodiments. Those skilled in the art may envision other embodiments and variations of the invention which fall within the scope of the claims.

We claim:

1. A bromine- and chlorine-containing liquid prepared by a method, comprising:
   a. combining a source of bromine ions, hydrogen peroxide and a complexing agent;
   b. adding a first alkaline source and a solid organic chlorinating agent;
   c. conducting a solid-liquid separation; and
   d. adding a second alkaline source, to form a bromine- and chlorine-containing liquid.

2. A bromine-containing liquid prepared by a method, comprising:
   a. combining a source of bromide ions, a complexing agent, and a solid organic halogenating agent;
   b. conducting a solid-liquid separation; and
   c. adding an alkaline source, to form a bromine-containing liquid.

3. A bromine-containing liquid, prepared by the method of claim 2, prepared to contain less than one mole of dissolved halide ion salts per mole of active halogen.

4. A bromine- and chlorine-containing liquid prepared by a method, comprising:
   a. combining a source of bromide ions, a complexing agent, and a solid organic chlorinating agent;
   b. conducting a solid-liquid separation; and
   c. adding an alkaline source, to form a bromine- and chlorine-containing liquid.

5. A bromine- and chlorine-containing liquid, prepared by the method of claim 1 or claim 4, having a total halogen content of at least about 2.25% when, expressed as $Br_2$ (1% when expressed as $Cl_2$).

6. The liquid of claim 5, having less than one mole of dissolved halide ion salts per mole of active halogen.

7. A bromine- and chlorine-containing liquid for microbiological control in industrial water systems, comprising the liquid of claim 5.

* * * * *